(12) United States Patent
Jalali et al.

(10) Patent No.: US 8,987,649 B2
(45) Date of Patent: Mar. 24, 2015

(54) METHODS FOR OPTICAL AMPLIFIED IMAGING USING A TWO-DIMENSIONAL SPECTRAL BRUSH

(71) Applicant: The Regents of the University of California, Oakland, CA (US)

(72) Inventors: Bahram Jalali, Los Angeles, CA (US); Keisuke Goda, Tokyo (JP); Kevin Kin-Man Tsia, Ma On Shan (HK)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/861,582

(22) Filed: Apr. 12, 2013

(65) Prior Publication Data

US 2014/0313310 A1    Oct. 23, 2014

Related U.S. Application Data

(62) Division of application No. 12/621,496, filed on Nov. 18, 2009, now Pat. No. 8,440,952.

(60) Provisional application No. 61/115,755, filed on Nov. 18, 2008, provisional application No. 61/115,770, filed on Nov. 18, 2008.

(51) Int. Cl.
    *H01L 27/00*    (2006.01)
    *H01L 31/00*    (2006.01)
    *G02B 21/36*    (2006.01)

(52) U.S. Cl.
    CPC .................................. *G02B 21/361* (2013.01)
    USPC ..................................... 250/208.1; 250/214.1

(58) Field of Classification Search
    CPC .................. H01L 27/14643; H01L 27/14609;
        H01L 27/14603; H01L 27/14645; H01L
        27/14647; H01L 27/14649; H01L 27/1465;
        H01L 27/14652; H01L 27/14665; H01L
        27/14667; H01L 27/14669; H01L 27/1467;
        H01L 27/148; H01L 27/14831; H01L
        27/14825; H04N 5/335
    USPC ............... 250/339.06, 337.07, 339.08, 208.1,
        250/214 R, 214.1, 226, 208.2, 237 G;
        356/326, 300, 301; 372/3, 6, 38.06;
        359/333, 334, 558, 566, 569, 599
    See application file for complete search history.

(56) References Cited

U.S. PATENT DOCUMENTS 5,121,231 A    6/1992    Jenkins et al.
5,315,423 A    5/1994    Hong (Continued)

OTHER PUBLICATIONS

Brignon, A. et al.—"Large-filed-of-view, high-gain, compact diode-pumped Nd: YAG amplifier"—Optics Letters, vol. 22, No. 18, pp. 1421-1423, Sep. 1997.

(Continued)

*Primary Examiner* — Pascal M Bui Pho
(74) *Attorney, Agent, or Firm* — John P. O'Banion

(57) ABSTRACT

An apparatus and method for ultrafast real-time optical imaging that can be used for imaging dynamic events such as microfluidics or laser surgery is provided. The apparatus and methods encode spatial information from a sample into a back reflection of a two-dimensional spectral brush that is generated with a two-dimensional disperser and a light source that is mapped in to the time domain with a temporal disperser. The temporal waveform is preferably captured by an optical detector, converted to an electrical signal that is digitized and processed to provide two dimensional and three dimensional images. The produced signals can be optically or electronically amplified. Detection may be improved with correlation matching against a database in the time domain or the spatial domain. Embodiments for endoscopy, microscopy and simultaneous imaging and laser ablation with a single fiber are illustrated.

6 Claims, 19 Drawing Sheets

(56) References Cited

U.S. PATENT DOCUMENTS

| | | | |
|---|---|---|---|
| 5,999,320 | A | 12/1999 | Shirasaki |
| 6,023,355 | A | 2/2000 | Bashaw et al. |
| 6,028,706 | A | 2/2000 | Shirasaki et al. |
| 6,341,036 | B1 | 1/2002 | Tearney et al. |
| 6,441,892 | B2 | 8/2002 | Xiao |
| 6,556,320 | B1 | 4/2003 | Cao |
| 6,831,781 | B2 | 12/2004 | Tearney et al. |
| 7,812,311 | B2 * | 10/2010 | DeCamp et al. ......... 250/339.07 |
| 7,898,656 | B2 * | 3/2011 | Yun et al. ...................... 356/300 |
| 8,440,952 | B2 | 5/2013 | Jalali |
| 2006/0203344 | A1 | 9/2006 | Miura et al. |
| 2007/0081236 | A1 | 4/2007 | Tearney et al. |
| 2009/0040516 | A1 | 2/2009 | Fritz et al. |
| 2011/0168776 | A1 * | 7/2011 | Jalali et al. .................... 235/385 |

OTHER PUBLICATIONS

Raghunathan, V. et al.—"Self-imaging silicon Raman amplifier"—Optics Express 15, pp. 3396-3408, 2007.

Hansch, T.W. et al.—"Image Amplification by Dye Lasers"—Applied Physics Letters, vol. 18, No. 4, pp. 108-110, Feb. 1971.

Akins, R. et al.—"Coherent optical image amplification by an injection-locked dye amplifier at 632.8 nm"—Applied Physics Letters 25, No. 9, pp. 660-663, Nov. 1979.

Tearney, G.J. et al.—"Spectrally encoded miniature endoscopy"—Optics Letters, vol. 27, No. 6, pp. 412-414, Mar. 2002.

Yelin, D. et al.—"Spectral-domain spectrally-encoded endoscopy"—Optics Express, vol. 15, No. 5, pp. 2432-2444, Mar. 2007.

Yelin, D. et al.—"Large area confocal microscopy"—Optics Letters, vol. 32, No. 9, pp. 1102-1104, May 2007.

Yelin, D. et al.—"Three-dimensional miniature endoscopy"—Nature, vol. 443, pp. 765, Oct. 2006.

Yelin, D. et al.—"Three-dimensional imaging using spectral encoding heterodyne interferometry"—Optics Letters, vol. 30, No. 14, pp. 1794-1796, Jul. 2005.

Xie, T. et al.—"Fiber-optic-bundle-based optical coherence tomography"—Optics Letters, vol. 30, No. 14, pp. 1803-1805, Jul. 2005.

Gmitro, A.F. et al.—"Confocal microscopy through a fiber-optic imaging bundle"—Optics Letters, vol. 18, No. 8, pp. 565-567, Apr. 1993.

Patterson, P.R. et al.—"A Scanning Micromirror with Angular Comb Drive Actuation"—Proc. 15th IEEE Int. Conf. on MEMS, Las Vegas, Nevada, Jan. 20-24, 2002, pp. 544-547.

Tran, P.H. et al—"In vivo endoscopic optical coherence tomography by use of a rotational microelectromechanical system probe"—Optics Letters, vol. 29, No. 11, pp. 1236-1238, Jun. 2004.

Liu, X. et al.—"Rapid-scanning forward-imaging miniature endoscope for real-time optical coherence tomography"—Optics Letters, vol. 29, No. 15, pp. 1763-1765, Aug. 2004.

Goda, K. et al.—"Amplified dispersive Fourier-transform imaging for ultrafast displacement sensing and barcode reading"—Applied Physics Letters 93, pp. 131109-1 through 131109-3, 2008.

Diddams, S.A. et al—"Molecular fingerprinting with the resolved modes of a femtosecond laser frequency comb"—Nature Letters, vol. 445, pp. 627-630, Feb. 2007.

Thorpe, M.J. et al.—"Cavity-enhanced optical frequency comb spectroscopy: application to human breath analysis"—Optics Express, vol. 16, No. 4, pp. 2387-2397, Feb. 2008.

Xiao, S. et al.—"2-D wavelength demultiplexer with potential for 1000 channels in the C-band"—Optics Express, vol. 12, No. 13, pp. 2895-2902, Jun. 2004.

Shirasaki, M.—"Large angular dispersion by a virtually imaged phased array and its application to a wavelength demultiplexer"—Optics Letters, vol. 21, No. 5, pp. 366-368, Mar. 1996.

Fang, N. et al.—"Sub-Diffraction-Limited Optical Imaging with a Silver Superlens"—Science, vol. 308, pp. 534-537, Apr. 2005.

Valentine, J. et al.—"Three-dimensional optical metamaterial with a negative refractive index"—Nature Letters, vol. 455, pp. 376-379, Sep. 2008.

Bartelt, H.O.—"Wavelength Multiplexing for Information Transmission"—Optics Communications, vol. 27, No. 4, pp. 365-368, Dec. 1978.

Shi, K. et al.—"Wavelength division multiplexed confocal microscopy using supercontinuum"—Optics Communications vol. 263, Issue 2, pp. 156-162, Jul. 2006.

Shi, K. et al.—"Chromatic confocal microscopy using supercontinuum light"—Optics Express, vol. 12, No. 10, pp. 2096-2101, May 2004.

Tai, A.M.—"Two-dimensional image transmission through a single optical fiber by wavelength-time multiplexing"—Applied Optics, vol. 22, No. 23, pp. 3826-3832, Dec. 1983.

Mendlovic, D. et al.—"Wavelength-multiplexing system for single-mode image transmission"—Applied Optics, vol. 36, No. 32, pp. 8474-8480, Nov. 1997.

Paek, E.G. et al.—"All-optical image transmission through a single-mode fiber"—Optics Letters, vol. 17, No. 8, pp. 613-615, Apr. 1992.

Oshita, Y. et al.—"Ultrafast Time-to-Two-Dimensional-Space Conversion System Using SHG Crystal"—Optics Review, vol. 9, No. 4, pp. 141-145, 2002.

Konishi, T. et al.—"Encrypted ultra-fast image transmission using an OTDM/WDM scheme"—Journal of Optics A: Pure and Applied Optics, vol. 5, pp. S365-S369, 2003.

Konishi, T. et al.—"Ultrafast image transmission by optical time-to-two-dimensional-space-to-time-to-two-dimensional-space conversion"—Journal of the Optical Society of America, vol. 16, No. 5, pp. 1076-1088, May 1999.

Oshita, Y. et al.—"Application of Ultrafast Time-to-Two-Dimensional-Space-to-Time Conversion (II): Time-Varying Spectral Control for Arbitrary Ultrafast Signal Reshaping"—IEEE Photonics Technology Letters, vol. 16, No. 2, pp. 623-625, Feb. 2004.

Iwamoto, K. et al.—"Two-dimensional image transmission based on the ultrafast optical data format conversion between a temporal signal and a two-dimensional spatial signal"—Applied Optics, vol. 40, No. 35, pp. 6527-6534, Dec. 2001.

Chang, T. Y. et al.—"One-way image transmission and reconstruction through a thick aberrating medium by use of volume holography"—Journal of the Optical Society of America, vol. 11, No. 12, pp. 3206-3211, Dec. 1994.

Luo, Y. et al.—"Laser-induced fluorescence imaging of subsurface tissue structures with a volume holographic spatial-spectral imaging system"—Optics Letters, vol. 33, No. 18, pp. 2098-2100, Sep. 2008.

Friesem, A.A. et al.—"Parallel Transmission of Images Through Single Optical Fibers"—Proc. of the IEEE, vol. 74, No. 2, Feb. 1983.

Volkmer, A. et al.—"Time-resolved coherent anti-Stokes Raman scattering microscopy: Imaging based on Raman free induction decay"—Applied Physics Letters, vol. 80, No. 9, pp. 1505-1507, Mar. 2002.

Potma, E.O. et al.—"CARS Microscopy for Biology and Medicine"—Optics & Photonics News, pp. 41-40-45, Nov. 2004.

Siders, C.W. et al.—"Detection of Nonthermal Melting by Ultrafast X-ray Diffraction"—Science, vol. 286, pp. 1340-1342, Nov. 1999.

Barty, A. et al.—"Ultrafast single-shot diffraction imaging of nanoscale dynamics"—Nature Photonics Letters, vol. 2, pp. 415-419, Jul. 2008.

Dong, C.Y.—"Fluorescence Lifetime Imaging by Asynchronous Pump-Probe Microscopy"—Biophysical Journal, vol. 69, pp. 2234-2242, Dec. 1995.

Buehler, C. et al.—"Time-Resolved Polarization Imaging by Pump-Probe (Stimulated Emission) Fluorescence Microscopy"—Biophysical Journal, vol. 79, pp. 536-549, Jul. 2000.

Choi, B.C. et al.—"Ultrafast Magnetization Reversal Dynamics Investigated by Time Domain Imaging"—Physical Review Letters, vol. 86, No. 4, pp. 728-731, Jan. 2001.

Evans, R.—"Pump-probe imaging of nanosecond laser-induced bubbles in agar gel"—Optics Express, vol. 16, No. 10, pp. 7481-7492, May 2008.

(56) References Cited

OTHER PUBLICATIONS

Porneala, C. et al.—"Observation of nanosecond laser-induced phase explosion in aluminum"—Applied Physics Letters, vol. 89, pp. 211121-1 to 211121-3, 2006.

Fetterman, H.R. et al.—"Real-time spectral analysis of far-infrared laser pulses using a SAW dispersive delay line"—Applied Physics Letters, vol. 34, No. 2, pp. 123-125, Jan. 1979.

Tong, Y.C. et al.—"Fibre dispersion or pulse spectrum measurement using a sampling oscilloscope"—Electronics Letters, vol. 33, No. 11, pp. 983-985, May 1997.

Kelkar, P.V. et al.—"Time-domain optical sensing"—Electronics Letters, vol. 35, No. 19, pp. 1661-1662, Sep. 1999.

Chou, J. et al.—"Time-Wavelength Spectroscopy for Chemical Sensing"—IEEE Photonics Technology Letters, vol. 16, No. 4, pp. 1140-1142, Apr. 2004.

* cited by examiner

METHODS FOR OPTICAL AMPLIFIED IMAGING USING A TWO-DIMENSIONAL SPECTRAL BRUSH

CROSS-REFERENCE TO RELATED APPLICATIONS

This application is a division of U.S. patent application Ser. No. 12/621,496 filed on Nov. 18, 2009, now U.S. Pat. No. 8,440,952, incorporated herein by reference in its entirety, which is a nonprovisional of U.S. provisional patent application Ser. No. 61/115,770 filed on Nov. 18, 2008, incorporated herein by reference in its entirety, and a nonprovisional of U.S. provisional patent application Ser. No. 61/115,755 filed on Nov. 18, 2008, incorporated herein by reference in its entirety.

STATEMENT REGARDING FEDERALLY SPONSORED RESEARCH OR DEVELOPMENT

This invention was made with Government support under H94003-07-2-0702, awarded by the U.S. Department of Defense, and N66001-07-1-2007, awarded by the U.S. Department of the Navy. The Government has certain rights in the invention.

INCORPORATION-BY-REFERENCE OF MATERIAL SUBMITTED ON A COMPACT DISC

Not Applicable

BACKGROUND OF THE INVENTION

1. Field of the Invention

This invention pertains generally to optical imaging devices and methods and more particularly to an apparatus and method for high-speed, real-time, two- and three-dimensional imaging enabled by optically amplified parallel to serial conversion. One embodiment of the method also uses active illumination of the object and provides a faster shutter speed, higher frame rate, and higher sensitivity than is capable in the art. Its applications include industrial inspection and monitoring, microscopy, and endoscopy both for industrial and medical uses.

2. Description of Related Art

The capability of real-time high-speed optical imaging is essential for capturing the evolution of dynamic events in a variety of systems and networks. For instance, in biomedical and clinical applications, there is an increasing need to study the transient dynamics of biomolecules. The time scale of these dynamic processes is usually on the order of nanoseconds or shorter. Likewise, achieving reliable real-time, high-speed optical microscopy is the key to studying and understanding ultrafast non-repetitive, transient chemical and biological processes such as molecular conformational changes, protein folding, apoptosis, myosin movement, and neural activity. Optical imaging with both high-speed and real-time imaging capabilities also allows high-throughput medical diagnostics such as cell-counting and the study of chemical signals between cells and within cells, and fault detection in the material testing industry.

Unfortunately, conventional detection techniques for imaging are slow and incapable of capturing dynamic processes that occur on the time scale of nanoseconds or shorter. This is due to the low frame rate of conventional image sensor arrays such as CCD and CMOS cameras in optical microscopes where the frame rate is typically 100 Hz-10 kHz. The speed is similar for the mechanically scanning laser scanners and for scanners where the microscope stage is scanned.

For CCD cameras, the low frame rate is partially due to the image download time. Because imaging requires data in two dimensions, downloading images from the CCD chip typically takes several milliseconds, while shutter speeds can be as short as 100 ns. In addition, conventional image sensor arrays such as COD's and CMOS cameras suffer from individual element mismatches—a problem that limits the dynamic range of the system. These mismatches are particularly difficult to calibrate when fast single-shot detection is desired. The problem is similar to the interchannel mismatch problem which limits the dynamic range of multi-channel analog-to-digital converters.

Due to limitations in scan rate, conventional optical imaging techniques are inadequate for probing ultrafast events, especially for non-repetitive transient phenomena. This is due to the fundamental trade-off between sensitivity and speed. Higher sensitivity requires longer integration time and therefore lower speeds. Although an ultra-high-speed CCD with a frame rate of 1 Mfps (frames per second) has been reported recently, this was achieved by cooling the detector array to reduce the thermal noise. However, cooling is undesirable as it requires a refrigeration unit to accompany the camera. Another technique that was used to reach 1 Mfps was the use of a high intensity illuminator. This is undesirable for many applications due to the potential damage to the sample (particularly true for biological samples) as well as eye safety concerns for the user.

Another approach to imaging fast events is based on the so-called time-resolved pump-probe technique that has been used to capture dynamic events with temporal resolution down to picoseconds. The basic principle of typical pump-probe measurements is the following: A sample is exposed to a pump pulse from a light source, which generates some type of excitation or modification in the sample. After an adjustable time delay (controlled with an optical delay line), a probe pulse is directed to the sample, and its reflection or transmission is measured. By monitoring the probe signal as a function of the time delay, it is possible to obtain information on the decay of the generated excitation, or on other processes initiated by the pump pulses. However, the temporal resolution is fundamentally limited by the pulse duration. This technique has different variants which are used for different purposes, such as time-resolved coherent anti-Stokes Raman scattering (CARS) microscopy, X-ray diffraction imaging, pump-probe fluorescence microscopy, time-resolved magneto-optical Kerr effect (MOKE) microscopy, and pump-probe shadowgraph imaging. Typically, the time delay can be precisely adjusted by varying the relative path difference between the pump and probe. However, the fact that this is not a real-time imaging approach requires repetitive measurements at different time delays in order to acquire a complete sequence of images revealing the dynamics of the triggered event. In practice, the image acquisition speed is primarily limited by the relatively slow mechanical movement of the mirror which provides the tunable time delay (on the order of 1 kHz).

Accordingly, there is a need for a system and method for real-time, high-speed optical imaging and microscopy that not only provides two dimensional or three dimensional imaging but can also be scaled or sized for use in a variety of applications ranging from medical and non-medical endoscopy to barcode reading. The present apparatus and methods satisfy these needs, as well as others, and are generally an improvement over the art.

BRIEF SUMMARY OF THE INVENTION

The present invention is an apparatus and method for high-speed, real-time, compact multi-dimensional spectrally encoded imaging which we call serial time-encoded amplified imaging (STEAD. The approach uses a two-dimensional spectral pattern as a probe beam and employs optical amplification to overcome the fundamental trade-off between sensitivity and speed. Its applications include high-speed microscopy, endoscopy, biopsy, barcode reading, displacement sensing, night vision, remote sensing, and so on. The two-dimensional spectral pattern is produced by a series of spatial dispersive elements. Depending on the optical configuration, the two or three-dimensional spatial information of a sample is encoded into the spectrum of the back-reflected light from the sample. An image of the sample is produced by decoding the spectrum. The high-speed image acquisition is enabled by the combination of the method of chirped wavelength encoding and electronic time-domain sampling (CWEETS) and optical image amplification, which will be described in detail below.

Furthermore, by probing the sample with the two-dimensional spectral brush, the method of the present invention does not require any mechanical scanning—ideal for high-speed, real-time imaging with a miniaturized, compact probe in (1) various scientific, medical, and industrial applications, (2) medical and non-medical endoscopic applications, and (3) infrared imaging and remote sensing. It will be seen that the apparatus and methods can be adapted for use in many different scientific, medical and industrial fields. Several examples of the scientific and medical applications are molecular conformational changes, protein folding, apoptosis, myosin movement, and neural activity. Examples of the industrial applications include barcode reading, displacement sensing for monitoring and inspection of products including pharmaceuticals, and CD/DVD/Blu-Ray reading. Medical endoscopic applications include esophagogastroduodenoscopy, colonoscopy, proctosigmoidoscopy, duodenoscope-assisted cholangiopancreatoscopy, endoscopic retrograde cholangiopancreatography (ERCP), intraoperative cholangioscopy, rhinoscopy, bronchoscopy, cystoscopy, colposcopy, hysteroscopy, falloscopy, laparoscopy, arthroscopy, thoracoscopy, mediastinoscopy, amnioscopy, fetoscopy, panendoscopy, laryngoscopy, esophagoscopy, etc.

Several examples of potential non-medical applications of the invention are architectural endoscopy, borescopy for internal inspection of complex technical systems, examination of improvised explosive devices by bomb disposal personnel, surveillance via tight spaces, and so on.

The methods of the present invention preferably include three important features. The first feature of the present invention is spectral encoding of spatial information into the back-reflection of an optical beam incident onto a sample by use of spatial dispersion. This feature has the effect of converting the two-dimensional spatial information of the sample to spectral modulation of a laser beam. It hence constitutes space-to-spectrum mapping.

The second important feature is the use of chirped wavelength encoding and electronic time-domain sampling (CWEETS) for multi-dimensional optical imaging with either a broadband pulse laser or a swept-frequency continuous-wave laser in one embodiment. In the case of a broadband pulse laser, the spectrum of an optical pulse is mapped into a temporal waveform before or after the sample using a temporally dispersive element. Together with the first feature, the apparatus serializes the two-dimensional spatial information of a sample to a single temporal waveform. In other words, it performs space-to-time mapping. The temporal waveform may be captured by a single photodetector and digitized by a digitizer for image processing in one embodiment. In the case of a swept-frequency continuous-wave laser, the frequency of the laser is chirped by an external function generator. Likewise, the temporal waveform may be captured by a single photodetector and digitized by a digitizer for image processing. In this case, a temporally dispersive element is not required.

The third important feature is optical image amplification to enhance the imaging sensitivity. This optical image amplification overcomes the fundamental trade-off between imaging sensitivity and scan rate.

Preferably, the spectral encoding of the two-dimensional spatial information of a sample into the spectrum of a broadband optical beam uses an optical source that can be either a broadband pulse laser or a swept-frequency continuous-wave laser. The two-dimensional spectral imaging is achieved by a new technique that uses a pair of orthogonally oriented coarse and fine dispersers that produce a two-dimensional spectral pattern called a spectral brush. With this technique, incident probe light is dispersed and separated by the dispersers into many sub-beams of different colors. In other words, the input spectrum is mapped into the spatial domain in a manner that the frequency chirp causes a two-dimensional raster scan of the sample. One example for the coarse and finer dispersers is the combination of a diffraction grating and a virtually-imaged phased array (VIPA), respectively. The VIPA is essentially a tilted Fabry-Perot cavity and has the advantage of large angular dispersion (more than 1-2°/nm) in contrast to the relatively small angular dispersion of a diffraction grating (~0.1°/nm). Once the spectral brushes are incident onto the sample, its spatial information is encoded into the spectrum of the back-reflected spectral brushes from the sample.

An example of the second feature of the present invention is the use of CWEETS for multi-dimensional spectrally encoded imaging. The chirped wavelength encoding and electronic time domain sampling (CWEETS) technique has been used in spectroscopic measurements for one-dimensional spectrally encoded imaging and optical coherence tomography and reflectometry where images of the sample are obtained by mechanically scanning the probe beam over the sample in the past. However, the present invention is significantly different from pump-probe imaging methods known in the art using some form of CWEETS sampling in that it is a real-time non-invasive imaging technique in the optical band with a single high-speed photodetector that enables real-time image processing. Without the need for a pump-probe configuration, the imaging method of the present invention is particularly useful for studying biological processes which are difficult to reproduce or not feasible in a pump-probe setting.

Furthermore, as a simple optical configuration, the method of the present invention is compatible with conventional techniques for microscopy, capable of observing ultrafast transient events on the microscale and potentially on the nanoscale when combined with sub-diffraction-limited imaging techniques based on plasmonic or metamaterial-based superlenses. A metamaterial is a composite material with negative refraction index—a feature which allows spatial resolution beyond the diffraction limit. It has been demonstrated that a super lens is capable of achieving ultrahigh spatial resolution (almost ten times smaller than with conventional diffraction-limited lenses). Combining it with the apparatus of the present invention, optical imaging with ultrafast, single-shot capability and ultrahigh spatial resolution can be attained simultaneously.

The function of CWEETS varies, depending on the type of the optical source: (1) a broadband pulse laser and (2) a swept-frequency continuous-wave laser. The former case is based on broadband optical pulses produced by an optical frequency comb—an optical spectrum that consists of equally spaced laser modes across the spectrum. In the case of a broadband pulse laser source, the function of CWEETS is preferably performed by pulse-by-pulse spectral analysis based on dispersive Fourier transformation—a powerful technique in which the spectrum of an optical pulse is mapped into a time-domain waveform using group-velocity dispersion. It replaces a diffraction grating and detector array with a dispersive fiber and single photodiode. This simplifies the system, and more importantly, enables fast real-time spectroscopic measurements (hence, fast real-time image acquisition). The function of CWEETS can be either before or after the sample.

In addition, the single photodiode detection enables imaging in the bands of the optical spectrum in which CCD's are incapable of detecting light. By performing a dispersive Fourier transformation on the optical pulses with a high dispersive fiber, their spectrum is decoded into a temporal waveform which is captured by a single photodiode, digitized by a digitizer, and signal-processed by a computer. Dispersive Fourier transformation based on the use of a broadband pulse laser is an important process of the spectral decoding (hence, image processing) and enables ultrafast real-time imaging at an image acquisition rate equal to the pulse repetition rate of the laser (typically on the order of tens of MHz). This is about two orders of magnitude faster than conventional image sensors such as CCD's and CMOS cameras in which downloading images from a CCD or CMOS chip typically takes several milliseconds to process although shutter speeds can be as short as 100 ns.

Furthermore, this method does not require any mechanical scanning for image acquisition. This technique promises an effective imaging method for ultrafast applications, especially biomedical applications, such as laser surgery, microfluidic biochips, molecular conformational changes, protein folding, apoptosis, myosin movement, and neural activity. One of the most important applications may be in hematology where current cytometry systems can count and classify large numbers of cells at a high rate (e.g. 30 seconds per samples, 5000 white cells) but they cannot perform imaging. On the other hand, imaging is important for morphological characterization, for example for distinguishing the normal (Segmented) and immature (e.g. band) white blood cells (neutrophil) as an indicator of infection. A high speed cell imaging system capable of delivering counting precision comparable to modern flow cytometers at the same sample throughput does not currently exist.

In the case of a swept-frequency continuous-wave laser optical source, the function of CWEETS is performed by chirping the frequency of the continuous-wave laser with an external function generator. The method of the present invention is a significant advance over the one-dimensional spectrally encoded imaging with a swept-frequency continuous-wave laser. In this prior art, two-dimensional scanning is achieved by mechanical movement in the second dimension. The present invention performs two-dimensional scanning without any mechanically moving parts by using a pair of orthogonally oriented spatial dispersers to create a two-dimensional spectral brush. By sweeping the frequency of the probe laser, the chirped frequency probe beam makes a raster scan on the sample. The back-reflected beam is collected and detected by a single photodetector, digitized by a digitizer, and processed by a computer. The signal from the function generator is used to calibrate the position of the probe light on the sample to construct an image. The technique of scanning the laser on the sample without mechanically scanning the probe is a key process that enables high-speed, real-time imaging. The image acquisition rate of the technique is equal to the period of the sweep function generated by the function generator and the frequency response of the laser (typically up to ~100 kHz). This technique may be useful for industrial applications such as barcode reading and displacement sensing as well as remote sensing and night vision.

Optical image amplification of weak signals (hence, images of the sample) to enhance the imaging sensitivity is another important feature of the invention. The space-to-time conversion performed by the combination of the first two features has the effect of serializing the two-dimensional spatial information of the sample and makes it possible to amplify the entire two-dimensional image, consisting of a two-dimensional array of pixels, using a single channel amplifier. With this approach, image amplification can now be performed using optical amplification techniques similar to that used in fiber optic communications. These include distributed Raman amplifiers or discrete optical amplifiers such as rare-earth doped fiber amplifiers (for example, erbium-doped fiber amplifiers) and semiconductor optical amplifiers. This approach makes image amplification significantly easier than with solid-state image amplifiers that possess the inherent problems of image distortion, low image gain, and low speed.

The optical post-amplification raises weak signals, which would otherwise be undetectable, well above the detection noise floor, and thus circumvents the fundamental trade-off between imaging sensitivity and scan rate. This results in enhanced imaging sensitivity without sacrificing the scan rate. In the case of Raman amplification, amplification is achieved within the same medium (e.g. fiber) that performs temporal dispersion (hence spectrum-to-time mapping). As demonstrated below, the optical post-amplification in the dispersive element compensates for the detrimental optical loss in the various dispersive elements in the imaging system associated with extrinsic propagation losses as well as the fundamental loss imposed by the Kramers-Kronig relations. Because of its distributed nature, Raman amplification results in the lowest noise figure when dispersive Fourier transformation is used to perform the spectrum-to-time conversion and is therefore preferred.

The desirable features for the temporal dispersive element are high total dispersion, low loss, large optical bandwidth, smooth dispersion over the bandwidth, and commercial availability. Dispersion compensation fiber (DCF) offers an optimum combination of these parameters at present. Chirped fiber Bragg gratings (CFBG's) offer lower loss per amount of dispersion and are more compact. However, they have less bandwidth and have undesirable group delay ripples. The group delay ripples can be partially compensated using digital signal processing. In general, with improvement in technology, the performance of CFBG's is expected to improve to the point that they will become competitive to DCF.

While the optical gain can also be achieved by discrete optical amplifiers such as erbium-doped fiber amplifiers (EDFA's) and semiconductor optical amplifiers, distributed Raman amplification within the dispersive fiber (or an integrated waveguide) is superior because it maintains a relatively constant signal level throughout the dispersive Fourier transformation process. This important property maximizes the signal-to-noise-and-distortion ratio by keeping the signal power away from low power (noisy) and high power (nonlinear distortion) regimes. In addition to a lower noise figure, Raman amplification also has a more flexible gain spectrum than semiconductor amplifiers or EDFAs where, in an amorphous medium such as glass, it is naturally broadband. The gain spectrum can be further broadened by using multi-wavelength pump lasers, and, surprisingly but fortuitously, extremely broadband gain spectra can be realized using incoherent pump sources. This is highly desirable because a large optical bandwidth results in a large number of pixels in the imaging method of the present invention. Raman-amplified dispersive elements also eliminate the need for a high power optical source.

Alternatively, the described features of the present invention can be combined with an interferometric configuration to perform three-dimensional imaging without any mechanical scanning within the probe. The term, "three-dimensional" refers to the two-dimensional transverse dimensions as well as the axial dimension. In this method, the axial information of a sample is obtained in an analogous manner to that in time-domain optical coherence tomography. A rapidly scanning time delay is employed in one of the interferometer arms (called the reference arm) whereas the other arm (called the sample arm) is used for probing the sample. Here the type of the interferometer may be either a Michelson interferometer or a Mach-Zehnder interferometer, for example.

One method of the present invention is an extension of the one-dimensional spectrally encoded imaging to two-dimensional spectrally encoded imaging together with CWEETS, enabling high-speed three-dimensional imaging without any mechanical scanning within the probe. Without a need for mechanical scanning within the probe, the technique provides reduced size and enhanced flexibility. These properties are extremely useful for endoscopy in which the small size and flexibility of the endoscopic probe are required to reduce requirements for anesthesia and minimize tissue damage when inserted into very small regions. Finally, the spatial resolution obtained in the present invention, determined by the spectral resolving power of the dispersers, can be higher than that in optical fiber bundles.

Alternatively, the imaging apparatus of the present invention can be partly miniaturized into a millimeter-sized probe which can be used for endoscopy. Without a need for any mechanical scanning at the distal end of the probe, the endoscope can be more compact in size and flexible than conventional endoscopes. The diameter of the endoscopic probe can be as small as that of the optical fiber, which is typically in the range between 80-250 micrometers.

In another embodiment, the imaging apparatus of the present invention can be arranged to detect the transmission of the spectral brush incident on the sample instead of the reflection. There are a few potential optical configurations to measure the transmission: (1) by placing a mirror on the back of the sample so that the transmitted spectral brush returns to the spatial dispersers, and (2) by setting up an identical pair of spatial dispersers at the transmission and decoding the spectrally encoded spatial information of the sample with transmission optics instead of using an optical circulator. This method may be useful for observation of biological tissue or cells which tend to have low reflectance which makes it relatively difficult to probe biological samples with reasonable imaging sensitivity.

Another aspect of the present invention is to provide an apparatus and method for ultrafast optical correlation matched detection of measured images with a large image database. This can be employed in two-dimensional barcode reading applications, high-throughput biological cell-counting, such as screening of cancer cells, biochemical sensing, and combinatorial chemistry with high-throughput correlated matched detection. This scanning correlation matched detection can be performed at the laser repetition rate.

Alternatively, the two and three-dimensional imaging techniques of the present invention can be combined with laser ablation based on the use of a powerful continuous-wave or pulse laser on top of the spectral brush. Applications of the technique include laser therapy, laser cutting, and laser surgery. In this method, another laser source (which can be either a continuous-wave laser or a pulse laser) is combined via a fiber coupler or beam combiner with the spectral brush probe. A sample of interest is first being monitored with the spectral brush probe, while a targeted area of the sample within the probing area of the spectral brush is subject to the other laser with higher optical power, which can be used to heat up or ablate the targeted area with high precision without the need for mechanically scanning the probe or high-power laser.

The serial time-encoded amplified imaging (STEAD of the invention can also be extended to recovery of the optical phase for the purpose of phase sensitive imaging. This can be achieved by using optical heterodyne performed in the photodetector. Here two copies of the chirped waveform are created, preferably starting from the same source, or using a second source. One copy illuminates the object whereas the other copy is the reference beam. The two enter the photodetector with the same polarization and with a pre-determined relative delay. By virtue of the square law response of the photodetector, they beat against each other producing an intermediate frequency (IF) signal whose magnitude is equal to the chirp rate multiplied by the relative delay. The heterodyne process preserves the relative phase of the reflected optical beam. This way, both the amplitude and phase of the optical beam reflected from the image are obtained from the IF signal.

It is also possible to combine the proposed imaging method with spectroscopy to achieve chemically selective 2D imaging. This chemical mapping is best achieved using Raman or CARS spectroscopy. In this case, the spectral brush will serve as the pump beam. It's important to note that the use of Raman scattering here is separate from, and in addition to, the use of Raman amplification in the dispersive fiber. Here Raman scattering occurs on the sample and the scattered light is collected and analyzed for the purpose of identifying the chemical constituents of the sample. Because in Raman and CARS the scattering the scattered signal is always at a fixed wavelength offset from the pump, and because the spatial location where the pump is incident is known, then the location from which the scattered signal is emitted is also known. Therefore, one will be able to construct a 2D Raman or CARS map of the sample. A central challenge with Raman and CARS is the low conversion efficiency of the pump beam to Stokes (in the case of Raman) and anti-Stokes (in the case of CARS) photons. To overcome this, the use of Raman labels (Raman tags) are preferred. Here the labels are applied to the sample and will serve to enhance the emission through the SERS (Surface Enhanced Raman Scattering).

According to one aspect of the invention an apparatus an method is provided that permits two-dimensional or three-dimensional imaging by spectrally encoding spatial information from a sample into a back reflection of an optical beam incident to the sample with spatial dispersion and decoding to provide a digital signal that can amplified and enhanced to produce an image.

According to another aspect of the invention a spectral brush is provided that creates a spectrum that is mapped into time by a temporal disperser.

According to a further aspect of the invention an apparatus and method is provided that eliminates the need for mechanical scanning and is particularly suited for endoscopic and microsurgical applications.

Another aspect of the invention is to provide an apparatus and method that features simultaneous imaging and microsurgery using the same single fiber.

A further aspect of the invention is to provide an apparatus and method for ultrafast real-time optical imaging with a high frame rate that will permit imaging of dynamic events such as shock waves, microfluidics, surgical events and neural activity.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWINGS

The invention will be more fully understood by reference to the following drawings which are for illustrative purposes only.

DETAILED DESCRIPTION OF THE INVENTION

Referring more specifically to the drawings, for illustrative purposes the present invention is embodied in the methods generally shown in FIG. 1 through FIG. 4 and the associated devices that may be used to perform the methods shown in FIG. 5 through FIG. 19. It will be appreciated that the apparatus embodiments may vary as to configuration and as to details of the parts, and that the methods may vary as to the specific steps and sequence, without departing from the basic concepts as disclosed herein.

The present invention relates to devices and methods for two or three dimensional imaging illustrated by the use of a broadband laser pulse or swept-frequency continuous wave light sources and CWEETS. The devices and methods may also be combined with other devices and systems that utilize or can benefit from real time imaging.

Generally, the imaging is produced by generating a two-dimensional spectral brush with a two-dimensional disperser and a light source and exposing a sample. Spatial information of the sample is encoded into the spectrum of spectral brush to provide a back reflected spectral brush that is subsequently decoded with a temporal disperser and spectrometer to provide an electric signal which is processed to retrieve a two-dimensional digital image.

Figure 1:
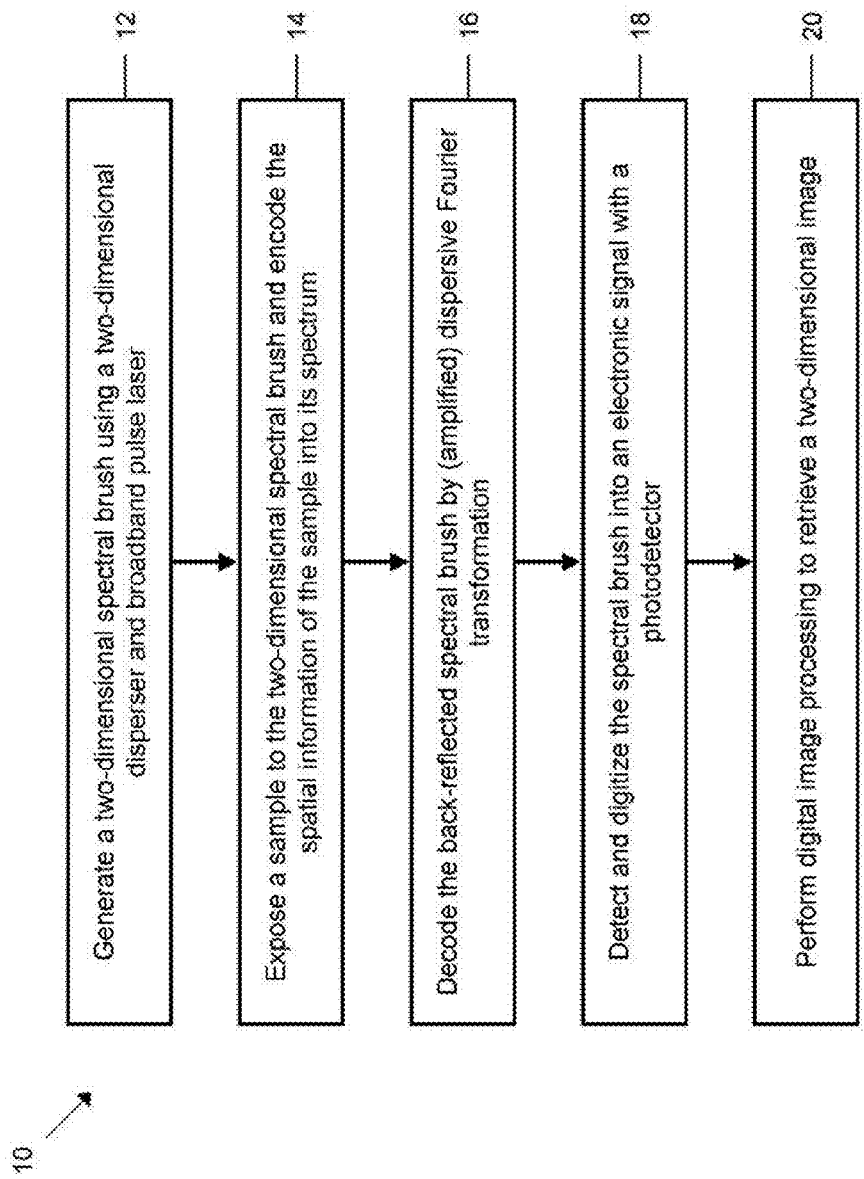
FIG. 1 is a flow chart of one embodiment of the method for optically amplified two-dimensional space-time imaging based on CWEETS with a broadband pulse laser.

Turning now to the flow diagram of FIG. 1, one method embodiment 10 of the invention is schematically shown. The illustrated method 10 is one adaptation of the invention for two-dimensional spectrally encoded imaging for microscopy and endoscopy where high-speed real-time image acquisition is needed. The method 10 provides imaging using CWEETS based on a preferably amplified dispersive Fourier transformation using a broadband pulse laser. In the embodiment shown in FIG. 1, at Block 12 a broadband laser pulse probe beam is first spatially dispersed by a pair of orthogonally oriented spatial dispersers in order to map the spectrum into a two-dimensional space in such a manner that the increasing frequency makes a raster scan on the sample. This two-dimensional pattern is referred to as a spectral brush. Examples of suitable spatial dispersers are diffraction gratings, prisms, and virtually-imaged phased arrays (VIPAs) and the like.

At Block 12, the broadband pulse laser is preferably a supercontinuum that is directed toward the sample. The supercontinuum may be created by passing a pulse laser with high peak power through a high nonlinearity fiber, for example. Alternatively, the optical source may be given by an ultra-short pulse laser with a large bandwidth such as a Titanium: Sapphire laser. The probe laser may also be optically amplified and filtered prior to the spatial dispersers. The bandwidth of the probe beam is preferably as large as possible because dispersion angles (related to the number of resolvable points in the acquired image) of the spatial dispersers such as diffraction gratings, prisms, and VIPAs increase with the input bandwidth. This means that larger bandwidth results in a larger field-of-view image or an image with higher spatial resolution for a given fixed field-of-view.

The broadband pulse laser beam is incident on a pair of orthogonally oriented spatial dispersers, e.g. diffraction gratings. One of the preferred configurations is that a diffraction grating provides coarse dispersion in one axis and a second diffraction grating provides fine dispersion in the other orthogonal axis. Hence, the spectral components of the probe beam are mapped into a two-dimensional space, forming a spectral brush.

At Block 14, the sample that is to be studied is exposed to the spectral brush created at Block 12. The spatial information of the sample, including the reflectivity profile of the sample, is encoded into the back-reflected spectral brush. The spectral brush created at Block 12 is focused by a lens onto the sample under test. The back-reflected spectral brush from the sample returns to the diffraction grating pair reforming a pulse. The back-reflected spectral brush contains the spatial information of the sample by spectrally encoding it into the spectral brush.

At Block 16, the back-reflected brush from the sample returns to the pair of the dispersers which reforms a short pulse and is thereafter converted into a time-domain waveform by a dispersive Fourier transformation. Since the spatial information of the sample is encoded in the spectrum of the pulse, the signal strength can easily be amplified by conventional optical amplifiers such as semiconductor optical amplifiers, rare-earth doped fiber amplifiers, and distributed Raman amplifiers as an optional step. Within the process of dispersive Fourier transformation, distributed Raman amplification can be performed to compensate for the detrimental loss in the dispersive element as well as propagation losses. With this configuration, the image can be amplified above the thermal noise level of the CCD, CMOS or infrared camera, and a drastic improvement in sensitivity can be achieved.

At Block 16 of FIG. 1, the dispersive element may be an optical fiber, a bulk crystal, a chirped mirror, or a chirped fiber Bragg grating etc. The dispersion produced by the dispersive element transforms the frequency-domain signal into a time-domain waveform. This process allows the constituent frequencies of the back-reflected spectral brush from the sample, which correspond to different points (pixels) of the sample image, to be temporally distributed in such a way that it allows different pixels of the image to be mapped into a time-domain waveform. During the Fourier transformation operation, the signal light may be optically amplified by stimulated Raman scattering when the dispersive element is optically pumped by broadband light or multiple continuous-wave lasers. Alternatively, the back-reflected light may be optically amplified by a Raman amplifier or a rare-earth doped fiber amplifier prior to the dispersive element which may or may not be optically amplified.

At Block 18, the converted time-domain optical waveform from Block 16 is detected by a photodetector that preferably converts the optical signal to an electronic signal. The electronic signal is then analyzed by a digital signal processor in the time domain. Each probe pulse, which represents an individual spectral brush, provides a snapshot of the sample at a specific point in time. The final image of the sample is retrieved by performing digital image processing on the collected electronic signal at Block 20. The image acquisition rate or scan rate is equivalent to the pulse repetition rate of the laser.

In order for the signal to be captured by an electronic digitizer or oscilloscope at Block 18, the time-domain waveform should preferably lie within the bandwidth per unit time for the waveform to be accurately represented. Therefore, the dispersion used to map the spectrum into a time-domain waveform should be sufficient to stretch the temporal waveform enough to be captured by the digitizer. In addition, if the single-shot data acquisition is desired, the digitizer must be capable of acquiring the necessary number of sampling points in a single-shot measurement.

Figure 2:
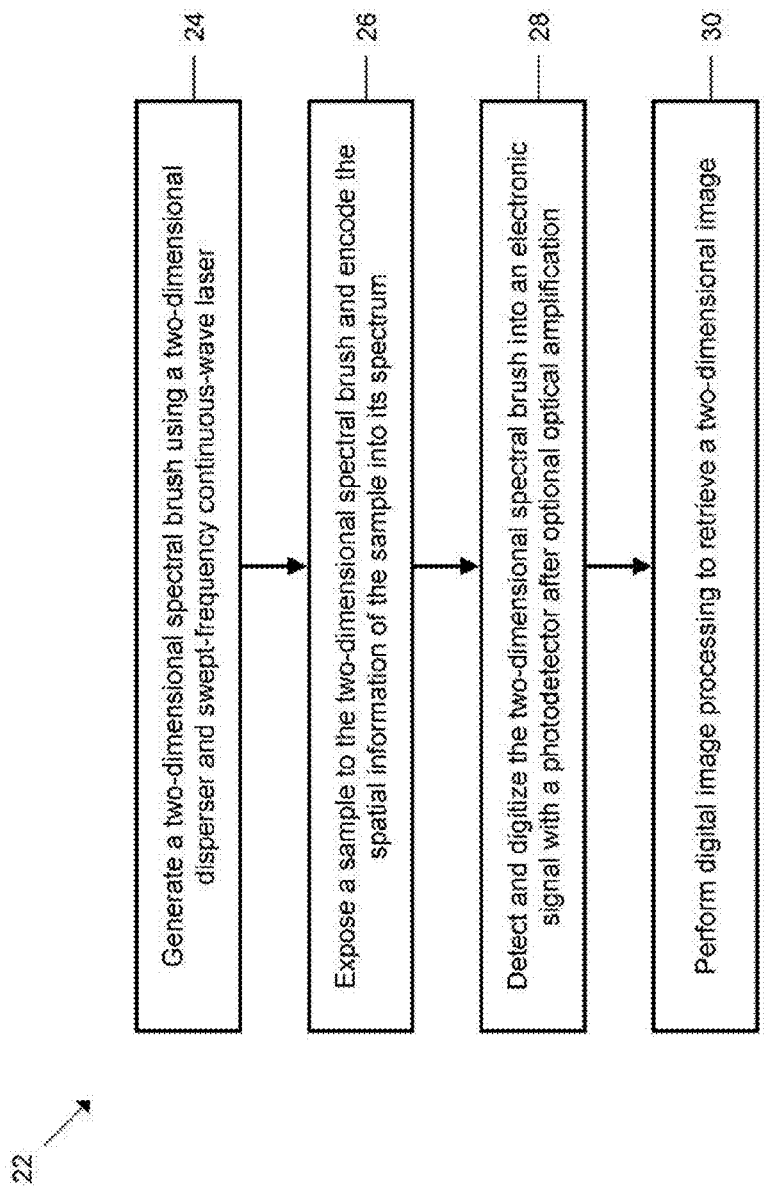
FIG. 2 is a flow chart of one embodiment of the method for optically amplified two-dimensional space-time imaging based on CWEETS with a swept-frequency continuous-wave laser.

Referring now to FIG. 2, a block diagram of one of the methods of the invention (Method 22) is shown that uses a swept-frequency continuous-wave laser as a light source. This method 22 is also applicable to two-dimensional spectrally encoded imaging for microscopy and endoscopy where high imaging sensitivity is required and not at the expense of high imaging speed.

In the embodiment of the method 22 shown in FIG. 2, a spectral brush is generated at Block 24. The procedure for generating the spectral brush is essentially the same as that shown at Block 12 of FIG. 1 with the only exception being that the optical source is a swept-frequency continuous-wave laser. The function of CWEETS is preferably implemented into the frequency sweeping of the laser. Just like at Block 12 in FIG. 1, the increasing frequency of the laser makes a raster scan on the sample, following the same frequency sequence in the spectral brush pattern generated at Block 12 in FIG. 1. Sweeping the frequency of the continuous-wave laser is essentially equivalent to chirping the frequency as a function of time.

At Block 26 in FIG. 1, the spatial information of the sample is encoded into the spectral components of the spectral brush. Block 26 is roughly the equivalent to Block 14 of FIG. 1. Optical post-amplification of the produced optical signal after the spectral encoding can optionally be performed to increase the detection sensitivity by employing broadband optical amplifiers such as Raman amplifiers, rare-earth doped fiber amplifiers, and semiconductor optical amplifiers.

At Block 28, the spectral brush is decoded by a photodetector and digitized by a digitizer into an electronic signal which is then subject to digital image processing to acquire an image of the sample. The details in this step are generally equivalent to those at Block 20 of FIG. 1.

Three dimensional images can also be produced using the methods of the invention. Generally the three dimensional images may be produced by generating a two-dimensional spectral brush with a two-dimensional disperser and a light source and exposing a sample to the spectral brush at locations in a third dimension in succession. Spatial information of the sample is encoded into its spectrum in an interferometric configuration to provide a back reflected spectral brush image at each location. The back reflected spectral brush images are preferably amplified and decoded with a spectrometer and processed to retrieve a final composite three-dimensional image.

Figure 3:
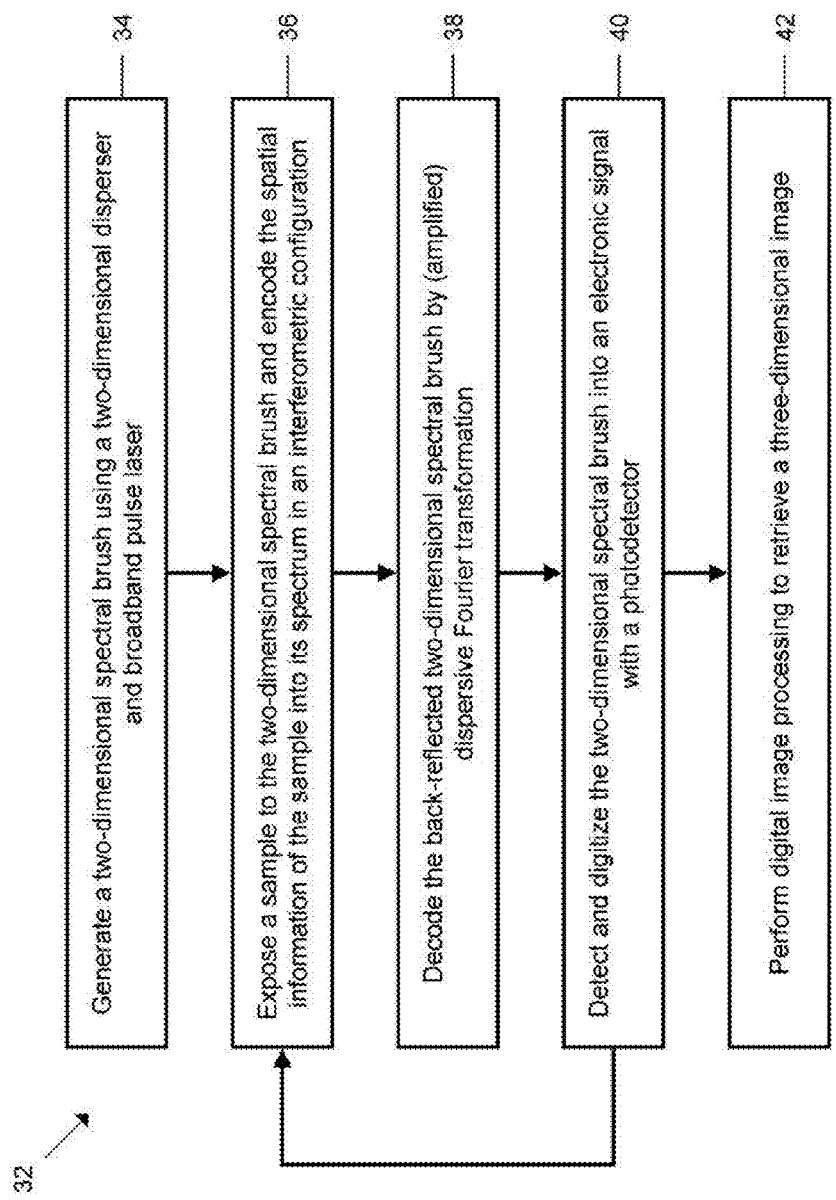
FIG. 3 is a flow chart of one embodiment of the method for three-dimensional space-time imaging based on CWEETS with a broadband pulse laser.

To illustrate, FIG. 3, shows a method 32 that is an extension of Method 10 to three-dimensional spectrally encoded imaging for microscopy and endoscopy using a broadband laser light source. In the embodiment shown, the spatial information of the sample in the third (z-axis) dimension (the depth information) other than the two lateral dimensions (x-axis and y-axis) is provided using an interferometric detection method. It requires forming an interferometer where the incident pulse is split into two arms: one called the sample arm for probing the sample and the other called the reference arm where no sample is present. The path length of the reference arm is translated longitudinally in time. For a broadband pulse laser as an optical source, low coherence interferometry is only achieved when the path difference between the sample and reference arms lies within the coherence length of the optical source. The envelope of this modulation changes as the path length difference is varied, where the peak of the envelope corresponds to path length matching. The peak of this envelope represents the location of the sample under test, with amplitude dependent on the reflectivity of the sample surface at that location.

This technique is analogous to optical coherence tomography. The main difference between the method of the present invention and optical coherence tomography is that no mechanical scanning at the probe is required to acquire a three-dimensional image while with optical coherence tomography mechanical scanning is required. This is chiefly due to the capability of encoding the spatial information of the sample in the lateral dimensions with the spectral brush at a high speed. The spectral brush can be generated by using a broadband pulse laser as shown at Block 34 of FIG. 3.

In order to acquire a full volumetric image, repetitive measurements are first needed to acquire the signals at different depths by varying the path difference between the reference and sample arms, that is, by performing the recurring operation from Block 36 to Block 40 in Method 32. The complete three-dimensional image of the sample is constructed by digital image processing at Block 42. In Method 32, the volumetric image acquisition speed is primarily limited by the mechanical movement of the mirror in the reference arm which can be up to 10 kHz. However, this speed can be increased by use of a high-speed phase modulator if the sample depth is not particularly large.

Figure 4:
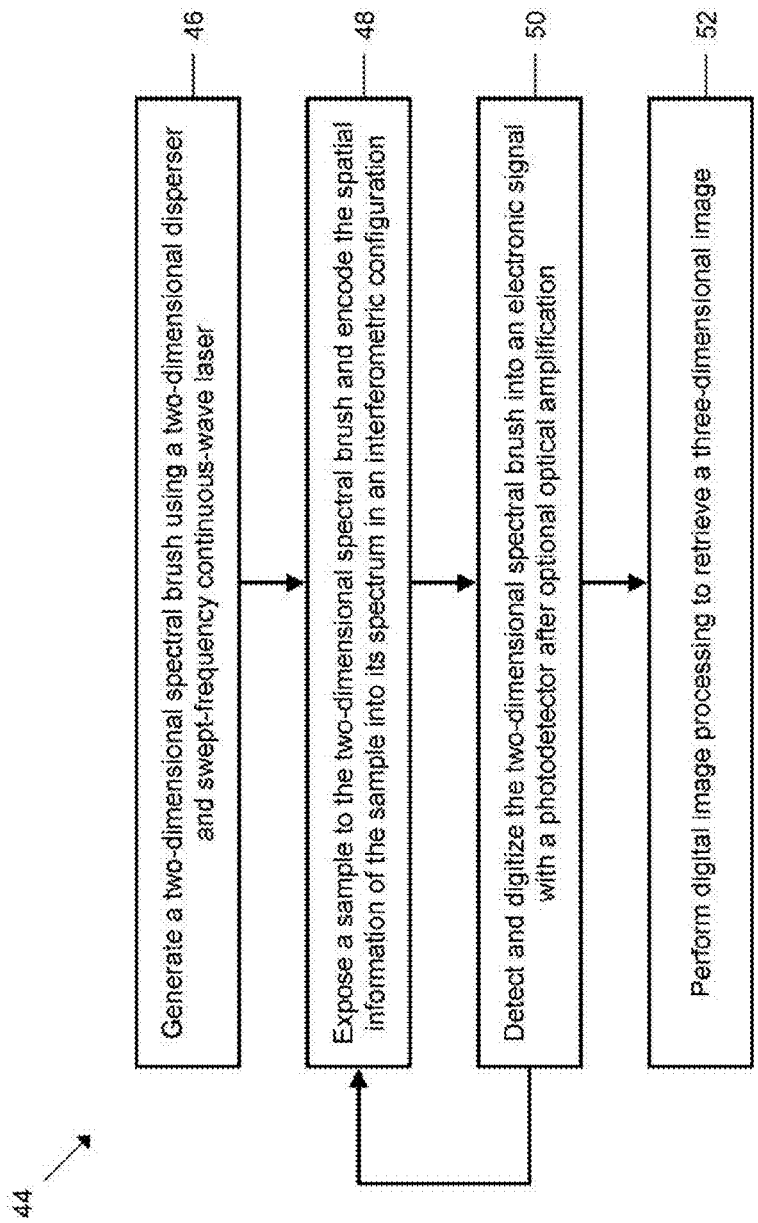
FIG. 4 is a flow chart of one embodiment of the method for three-dimensional space-time imaging based on CWEETS with a swept-frequency continuous-wave laser.

Likewise, the three dimensional imaging may be produced with a different light source. As shown in FIG. 4, the spectral brush can be generated by using a swept-frequency continuous-wave laser (at Block 46 in FIG. 4). In order to acquire a full volumetric image, repetitive measurements are first needed to acquire the signals at different depths by varying the path difference between the reference and sample arms, that is, by performing the recurring operation from Block 48 to Block 50 in Method 44. The complete three-dimensional image of the sample is constructed by digital image processing at Block 52. In Method 44, the volumetric image acquisition speed is primarily limited by the mechanical movement of the mirror in the reference arm which can be up to 10 kHz. However, this speed can be increased by use of a high-speed phase modulator if the sample depth is not large.

Figure 5:
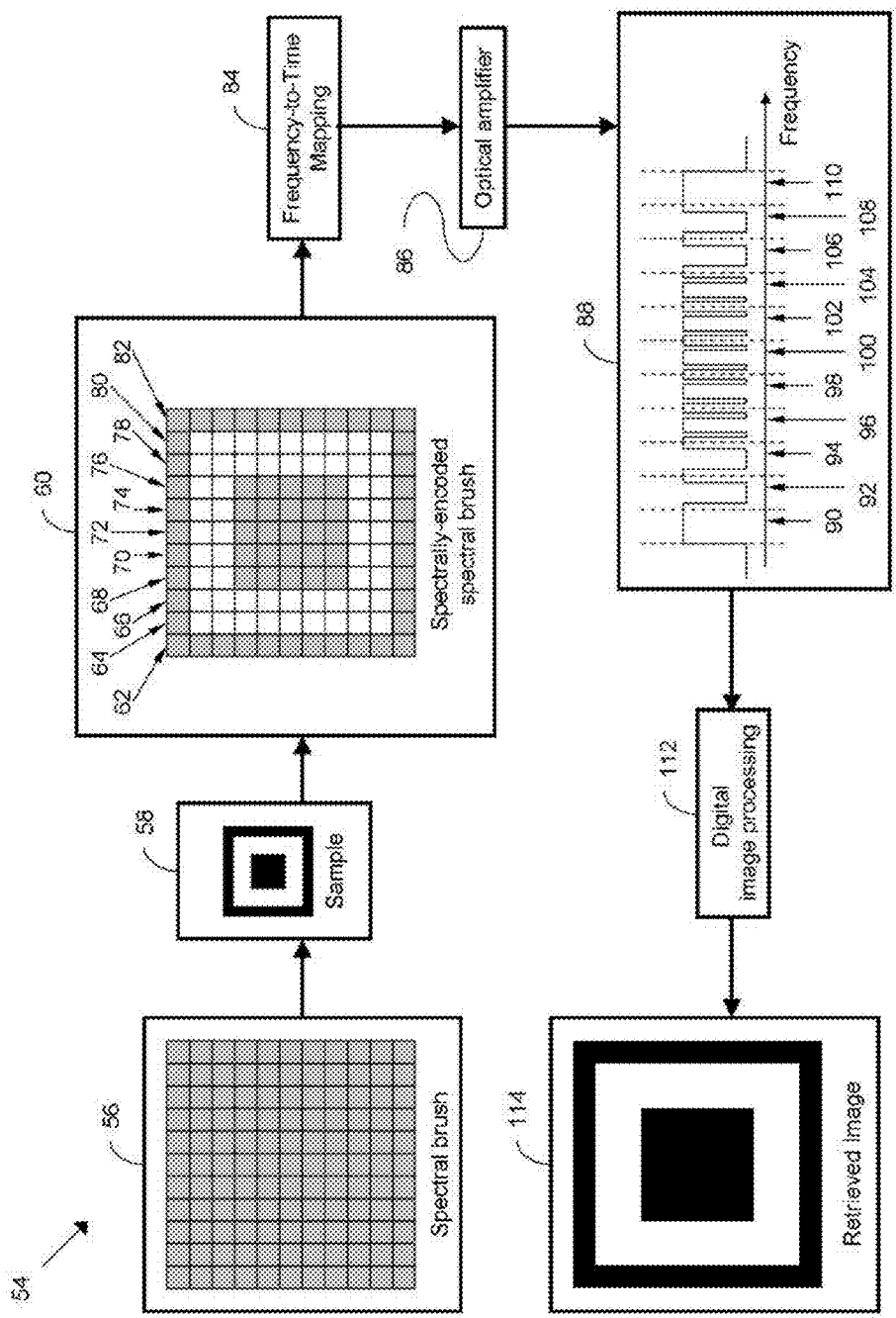
FIG. 5 is a conceptual block diagram of one embodiment of the image encoding and decoding system for optically amplified space-time imaging using a two-dimensional spectral brush according to the invention.

Referring now to FIG. 5, one embodiment of the procedure for encoding the spatial information of a sample under test into the spectrum of an incident spectral brush and decoding it by digital image processing into an image is shown is conceptually illustrated as Method 54 in FIG. 5. When the spectral brush 56 is incident to the sample 58, the back-reflected spectral brush 60 has the spatial information of the sample encoded into its spectrum. Note that the each grid in the spectral brush 56 and the back-reflected spectral brush 60 represents the finest resolvable image point primarily limited by the bandwidth of the digitizer if the dispersion is high enough such that the signal falls within the digitizer's bandwidth.

During the frequency-to-time mapping process (CWEETS) at block 84, the spatial information of the sample (encoded into the spectrum of the back-reflected spectral brush) is essentially unwrapped into a data array (serial data) after optical detection by a photodetector. The image encoded spectrum is subject to the broadband optical amplifier 86 to perform optical image amplification. More specifically, the spectrum 88 may be composed of a series of segments 90 to 110 which correspond to the spectral brush columns 62 to 82, respectively. Hence, the main task of the digital image processing 112 is to recover the original image 58 by carving the spectrum 88 into a number of segments (that correspond to a number of columns in the image) and putting them together to retrieve the image 114.

In addition, digital image processing 112 can be used to increase the signal-to-noise ratio by removing the noise components originating from detection noise (including shot noise and thermal noise), amplified spontaneous emission noise from the amplified dispersive element, the detrimental spectral non-uniformities or non-idealities of the probe beam from the electronic signal.

This method 54 may be used with Methods 10, 22, 32, and 44. Alternatively, in Method 54, the function of frequency-to-time mapping 84 can be before the spectral brush 56.

Figure 6:
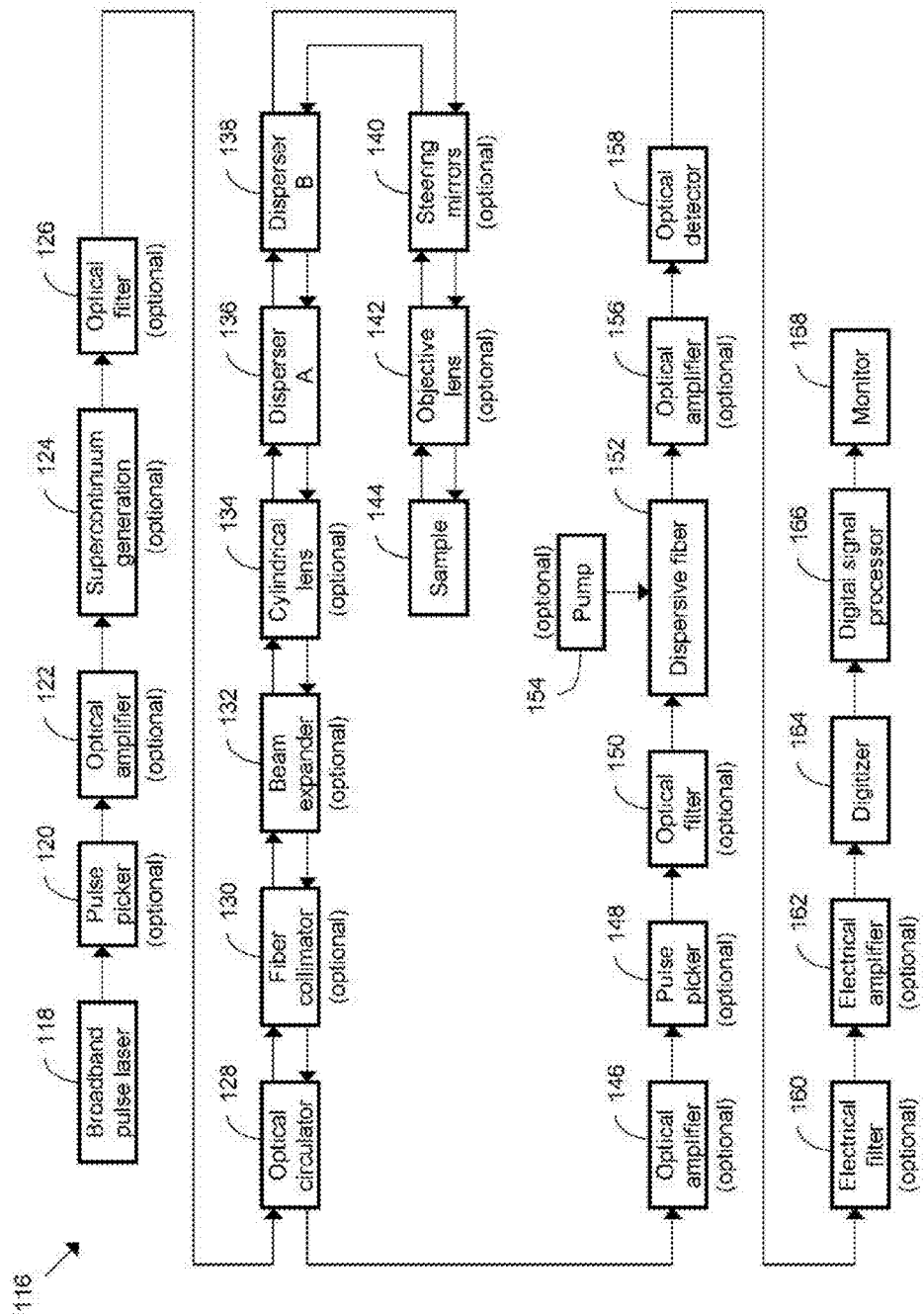
FIG. 6 is a schematic block diagram of one embodiment of an apparatus for optically amplified two-dimensional space-time imaging based on CWEETS using a broadband pulse laser and capable of performing the method shown in FIG. 1.

Referring now to FIG. 6, a schematic block diagram of one embodiment of an apparatus 116 that can perform the steps of Method 10 shown in FIG. 1. The optical source is a broadband pulse laser 118 which is subject to the optional pulse picker 120 and the optional optical amplifier 122. The spectrum of the laser can be broadened by the optional supercontinuum generator 124, which may be a high nonlinearity fiber. The optional optical filter 126 carves out the spectrum. The produced spectrum is directed toward the spectral brush generator which consists of disperser A 136 and disperser B 138. The fiber collimator 130, beam expander 132, and cylindrical lens or elliptical beam generator 134 are all optional. If the fiber collimator 130 is used, the collimator may act as an iris for confocal microscopy.

The produced spectral brush is incident onto the sample 144 via the optional steering mirrors 140 and objective lens 142. The back-reflected spectral brush, which contains the spatial information of the sample travels all the way back to the optical circulator 128 which directs the returned spectral brush toward the spectral decoder which mainly consists of the dispersive fiber 152 and the optical detector 158 with the optional optical amplifier 146, pulse picker 148, optical filter 150, and optical amplifier 156.

The dispersive fiber 152 may be optically pumped by the pump 154 to perform optical amplification in the fiber 152. Alternatively, the dispersive fiber 152 can be replaced with one or more dispersive elements (e.g. prisms, diffraction gratings, VIPAs, etc.). The optical amplification in the dispersive fiber 152 may be distributed Raman amplification. The dispersive fiber preferably performs (amplified) dispersive Fourier transformation that maps the spectrum of the back-reflected spectral brush into a temporal waveform which is captured by the optical detector 158. The electronic signal from the optical detector 158 is optionally filtered by the electrical filter 160 and amplified by the electrical amplifier 162. The signal is digitized by the digitizer 164 and then subject to digital image processing by the digital signal processor 166. The retrieved image is then displayed on the monitor 168 and may be stored.

In the embodiment of the apparatus 116, the disperser A 136 and disperser B 138 are orthogonally oriented so that the incident broadband pulse is transformed into a spectral brush. Disperser A 136 may be a coarse disperser while disperser B 138 may be a fine disperser. The arrangement of the dispersers 136 and 138 can also be reversed. One example for a coarse disperser is a diffraction grating or prism and an example for a fine disperser is a VIPA. The VIPA tends to have a higher diffraction angle (about ten times that of a typical diffraction grating), and is therefore desirable as one of the dispersers.

Additionally, if the pulse repetition rate of the laser is so high that temporally dispersed consecutive pulses get overlapped after the dispersive Fourier transformation that consists of the dispersive fiber 152, the effective rate can be reduced by the optional pulse picker 120 or 148.

The optional amplifier 122 may not be required if the initial laser pulse 118 is powerful enough to generate the supercontinuum. Also, if the initial pulse has a very large bandwidth, the optical amplifier 122 as well as the supercontinuum generator 124 may not be necessary. For example, Titanium:Sapphire mode-locked lasers can generate ultra-fast pulses (<10 fs) with extremely large bandwidth (>100 nm). The supercontinuum of radiation may be passed through the optional optical filter 126 to further carve out the spectrum.

The optical detector 158 is preferably used to convert the optical signal from the dispersive fiber 152 into an electronic signal. The optical detector 158 may be a photodiode or an avalanche photodetector. The electronic signal from the optical detector 158 may be filtered to limit its bandwidth (limiting the bandwidth to no more than is necessary to reduce electrical noise in the subsequent analog-to-digital conversion) by the optional electrical filter 160 and optionally amplified by the electrical amplifier 162. The signal may then be digitized by the digitizer 164. The signal may also be processed or analyzed with the digital signal processor 166 or computer and displayed and stored.

It can be seen that the methods implemented be apparatus 116 can utilized a large bandwidth of wavelengths for the probe beam. For example, high peak power probe pulses could be produced using a telecommunications laser or amplifier operating between 1300 and 1600 nm. It is also possible to frequency-double (by second-harmonic generation) or -triple (by third-harmonic generation) a telecommunications laser to produce higher frequencies for use in the apparatus. Another type of laser that could be used is the Titanium:Sapphire laser which offers ultra-short, high-power pulses at wavelengths between 650 and 1100 nm, usually in the vicinity of 800 nm. Although these laser types are preferred, other types of laser sources may also be used.

Figure 7:
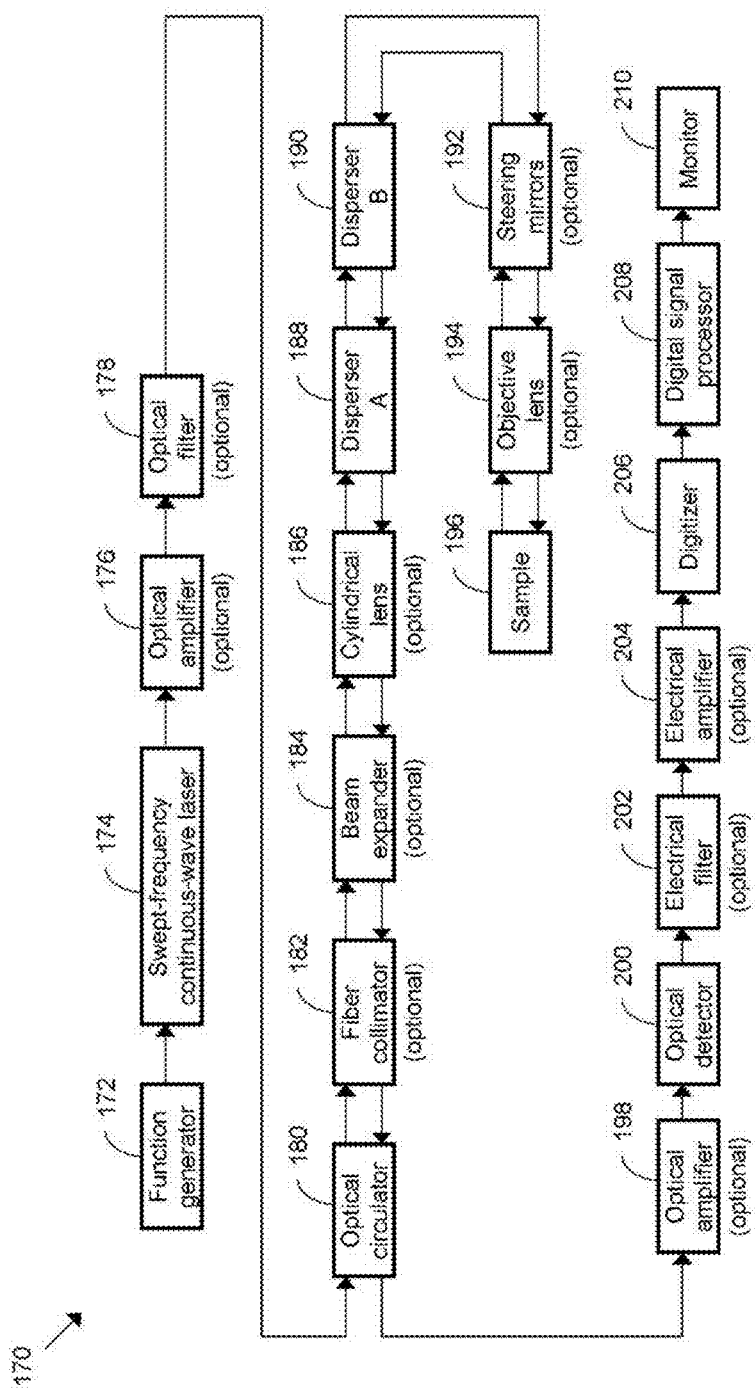
FIG. 7 is a schematic block diagram of one embodiment of an apparatus for optically amplified two-dimensional space-time imaging based on CWEETS using a swept-frequency continuous-wave laser and capable of performing the method shown in FIG. 2.

Referring now to FIG. 7, a schematic block diagram of one embodiment of an apparatus 170 that is capable of performing the method 22 of FIG. 2 is shown. In this apparatus 170, the function of CWEETS is performed by use of a swept-frequency continuous-wave laser and single photodetector instead of a broadband pulse laser and dispersive fiber that are shown in FIG. 6. The function generator 172 produces a sweep signal that drives the laser such that the frequency of the frequency-tunable continuous-wave laser 174 is swept over some bandwidth. The spectral brush pattern is generated by the dispersers A 188 and B 190, as described in relation to FIG. 6. The laser 174 makes a raster scan on the sample 196 when its frequency is swept, probing the spatial information of the sample 196 after being directed through the optional steering mirror 192 and optional optical lens 194. The back-reflected spectral brush from the sample via the optical circulator 180 is detected by the optical detector 200, which may be a photodiode. Although the combination of a spectrometer and a detector array can be used as an optical detector 200, a photodiode is preferred due to its fast response for high-speed image acquisition.

The rest of the digital image processing procedure is basically identical to that in FIG. 6 in the embodiment shown. The electronic signal from the optical detector 200 may be filtered to limit its bandwidth by the optional electrical filter 202 and optionally amplified by the electrical amplifier 204. The signal may then be digitized by the digitizer 206. The signal may also be processed or analyzed with the digital signal processor 208 or computer with programming and displayed on a monitor 210 and stored.

Figure 8:
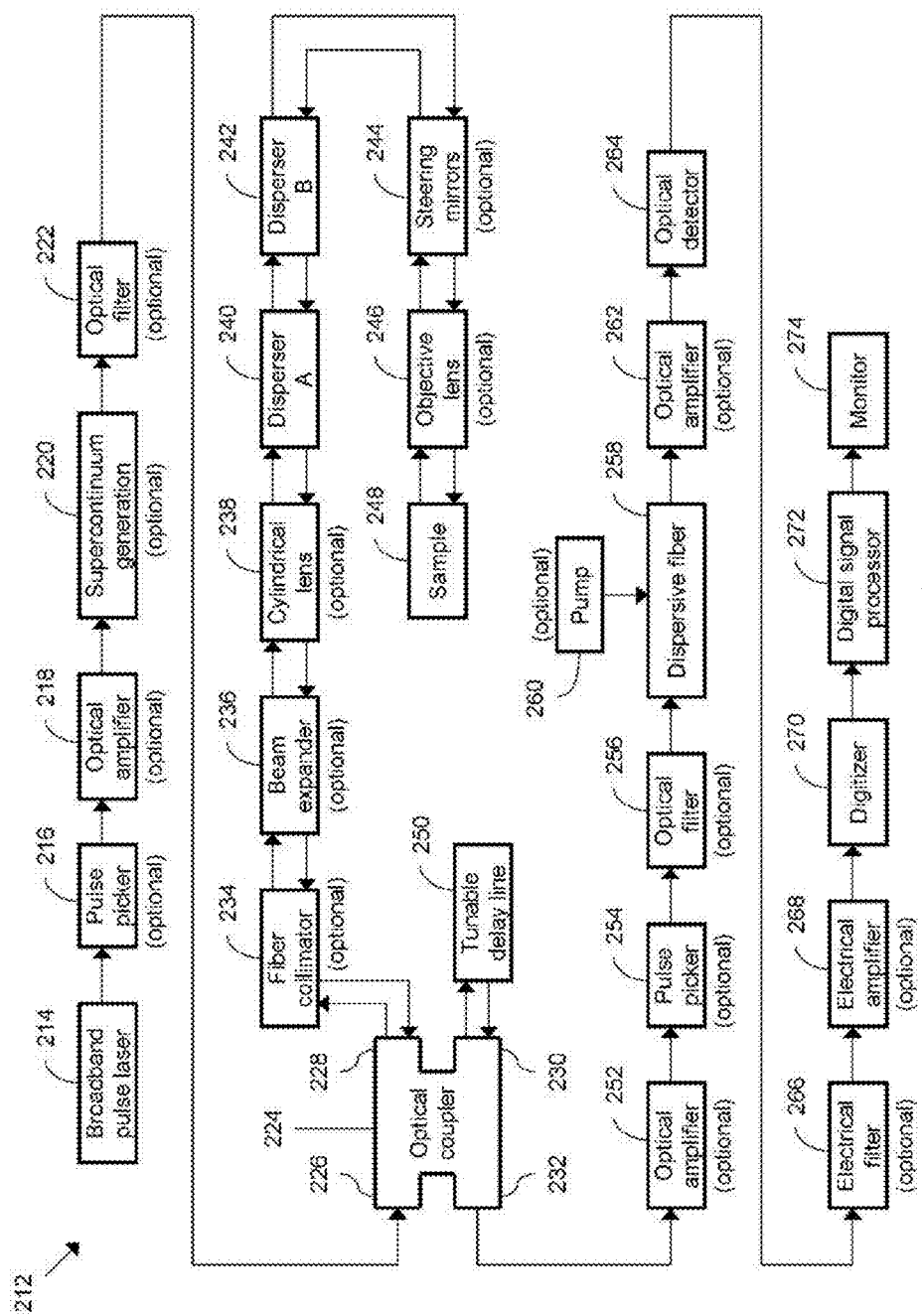
FIG. 8 is a schematic block diagram of one embodiment of an apparatus for three-dimensional space-time imaging based on CWEETS using a broadband pulse laser in an interferometric configuration capable of performing the method of FIG. 3.

Turning to FIG. 8, a schematic block diagram of one embodiment of an apparatus 212 that is configured to perform Method 32 shown in FIG. 3 is seen. The apparatus 212 is generally an extension of apparatus 116 shown in FIG. 6 to provide three-dimensional spectrally encoded imaging by using an interferometric configuration. Information of the sample in the third dimension (the depth information) is provided by forming an interferometer where one of the interferometer arms, called the sample arm, is used for probing the sample while the other arm is the reference arm.

A spectral brush is generated with a broadband pulse laser 214 optical source that is optionally subject to the pulse picker 216 and the optional optical amplifier 218. The spectrum of the laser can be broadened by the optional supercontinuum generator 220 that may consist of a high nonlinearity fiber. The optional optical filter 222 carves out the spectrum. The produced spectrum is directed toward an optical coupler 224 in the embodiment shown.

The optical coupler 224 may be a fiber coupler or beam splitter that consists of four ports 226, 228, 230, and 232. The input and output ports of the interferometer are the ports 226 and 232, respectively. The port for the sample arm is the port 228 while the port for the reference arm is the port 230. The interferometer may be, for example, a Michelson interferometer or a Mach-Zehnder interferometer.

The spectrum is directed through sample arm port 228 toward the spectral brush generator, which consists of disperser A 240 and disperser B 242, through the optional fiber collimator 234, beam expander 236, and cylindrical lens or elliptical beam generator 238. Sample 248 is exposed to the dispersed spectra through optional steering mirrors 244 and optical lens 246.

The path length of the reference arm is changed by the tunable delay line 250 which may be a mirror on top of a translation stage or piezoelectric transducer or a phase modulator with a mirror at the end of the interferometer arm. The translation stage, piezoelectric transducer, or phase modulator can be driven by an external function generator whose signal is used to calibrate the depth information of the sample 248 when digital image processing is performed. Using a broadband pulse laser 214 as an optical source, low coherence interferometry is achieved when the path difference between the sample and reference arms lies within the coherence length of the optical source. The envelope of this modulation changes as the path length difference is varied, where the peak of the envelope corresponds to path length matching. The peak of this envelope represents the location of the sample under test, with amplitude dependent on the reflectivity of the sample surface.

The signal from port 232 may be directed through the optical amplifier 252, pulse picker 254 and optical filter 256 to the dispersive fiber 258. CWEETS is performed by the dispersive fiber 258 which may be optically amplified in presence of the pump 260 in this embodiment. Optical detector 264 detects the amplified optical signal from the optional optical amplifier 262 and the resulting electrical signal can be improved by the optional electrical filter 266 and amplifier 268 and digitized by digitizer 270. By performing the loop from block 40 to block 36 in Method 32, the complete three-dimensional image of the sample is constructed by digital image processing 234 and the image may be viewed on monitor 326 and stored.

Figure 9:
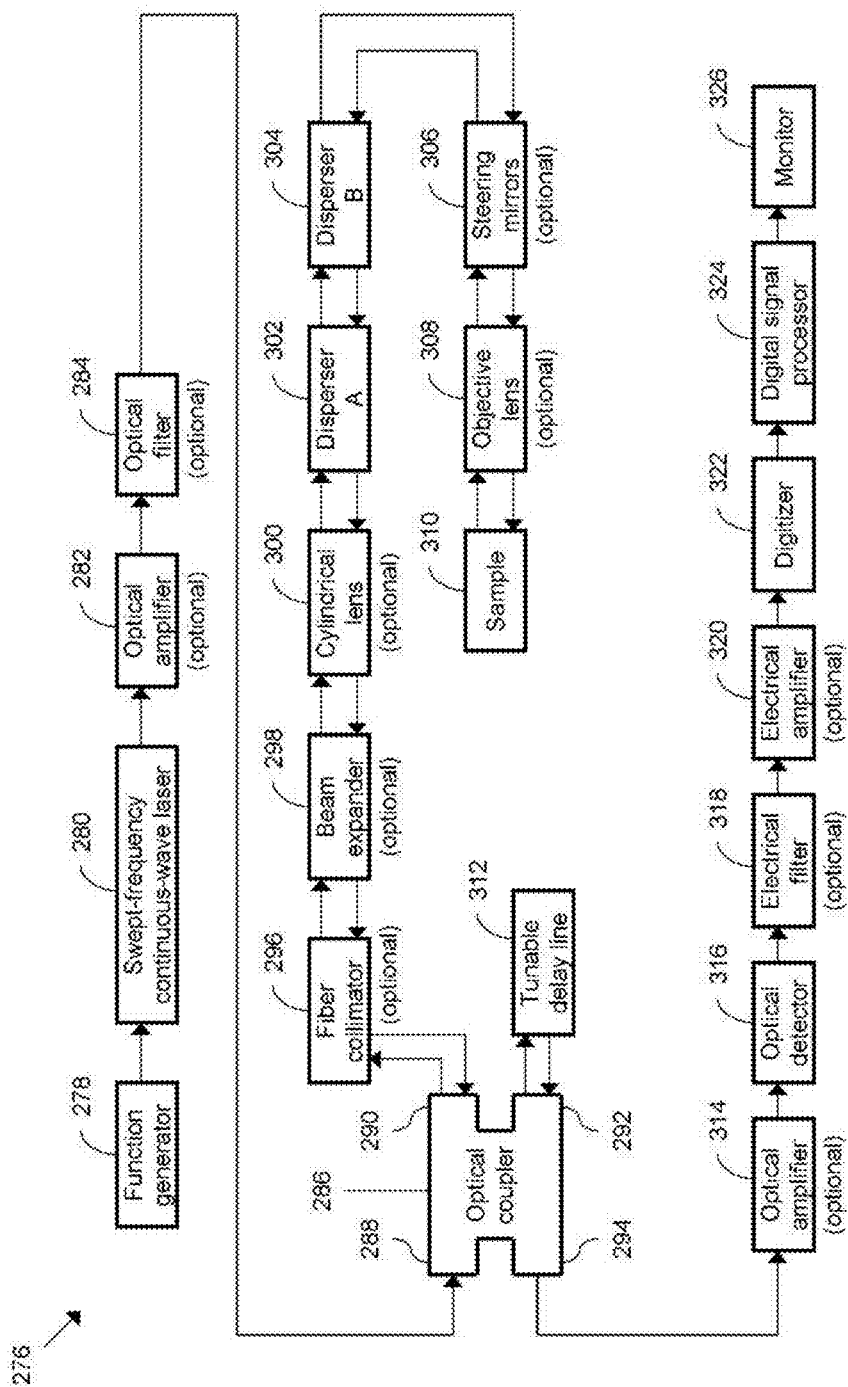
FIG. 9 is a schematic block diagram of one embodiment of an apparatus for three-dimensional space-time imaging based on CWEETS using a swept-frequency continuous-wave laser in an interferometric configuration and capable of performing the method of FIG. 4.

Referring now to FIG. 9, a schematic block diagram of one embodiment of an apparatus 276 for three dimensional imaging configured to perform the Method 44 shown in FIG. 4. The apparatus 276 is basically an adaptation of the apparatus 176 described in FIG. 7 to three-dimensional spectrally encoded imaging by use of an interferometric configuration. Information of the sample 310 in the third dimension (the depth information) is provided by forming an interferometer in which one of the interferometer arms called the sample arm is for probing the sample while the other is the reference arm.

The function generator 278 produces a sweep signal that drives the laser such that the frequency of the frequency-tunable continuous-wave laser 280 is swept over a selected bandwidth and optically amplified and filtered by optional optical amplifier 282 and optical filter 284. The spectral brush pattern is generated by the dispersers A 302 and B 304, from the beam directed through input port 288 and sample arm output port 290 of optical coupler 286 and the optional fiber collimator 296, beam expander 298 and cylindrical lens 300. The brush pattern may be directed to the sample 310 by optional steering mirrors 306 and objective lens 308.

The optical coupler 286 is preferably a fiber coupler or beam splitter with multiple ports 288, 290, 292 and 294. The interferometer may be a Michelson interferometer or a Mach-Zehnder interferometer, for example. The path length of the reference arm is changed by the tunable delay line 312 that may be a mirror on top of a translation stage or piezoelectric transducer or a phase modulator with a mirror at the end of the interferometer arm. The translation stage, piezoelectric transducer, or phase modulator can be driven by an external function generator whose signal is used to calibrate the depth information of the sample 310 when digital image processing is performed. Using a swept-frequency continuous-wave laser 280 as an optical source, low coherence interferometry is only achieved when the path difference between the sample and reference arms lies within the coherence length of the optical source. The envelope of this modulation changes as the path length difference is varied, where the peak of the envelope corresponds to path length matching. The peak of this envelope represents the location of the sample under test, with amplitude dependent on the reflectivity of the sample surface.

The composite optical signal is optionally amplified by the optical amplifier 314 and detected by the optical detector 316. The produced electrical signal is optionally filtered with an electrical filter 318 and amplified with an amplifier 320. Eventually the electrical signal is digitized with digitizer 322 and processed with digital signal processor 324 and observed on monitor 326 and thereafter stored.

The function of CWEETS is performed by use of the function generator 278 that changes the frequency of the laser 280. By performing the loop between block 50 and block 48 in Method 44 of FIG. 4, the complete three-dimensional image of the sample is constructed by digital image processing.

It will be seen that the methods described in FIGS. 1-4 and the illustrative devices applying the methods shown in FIGS. 5-9, can be adapted to specific diagnostic systems known in the art. For example, a schematic block diagram of one embodiment of an apparatus 328 using the method 10 shown in FIG. 1 that is configured for endoscopy is shown in FIG. 10.

Figure 10:
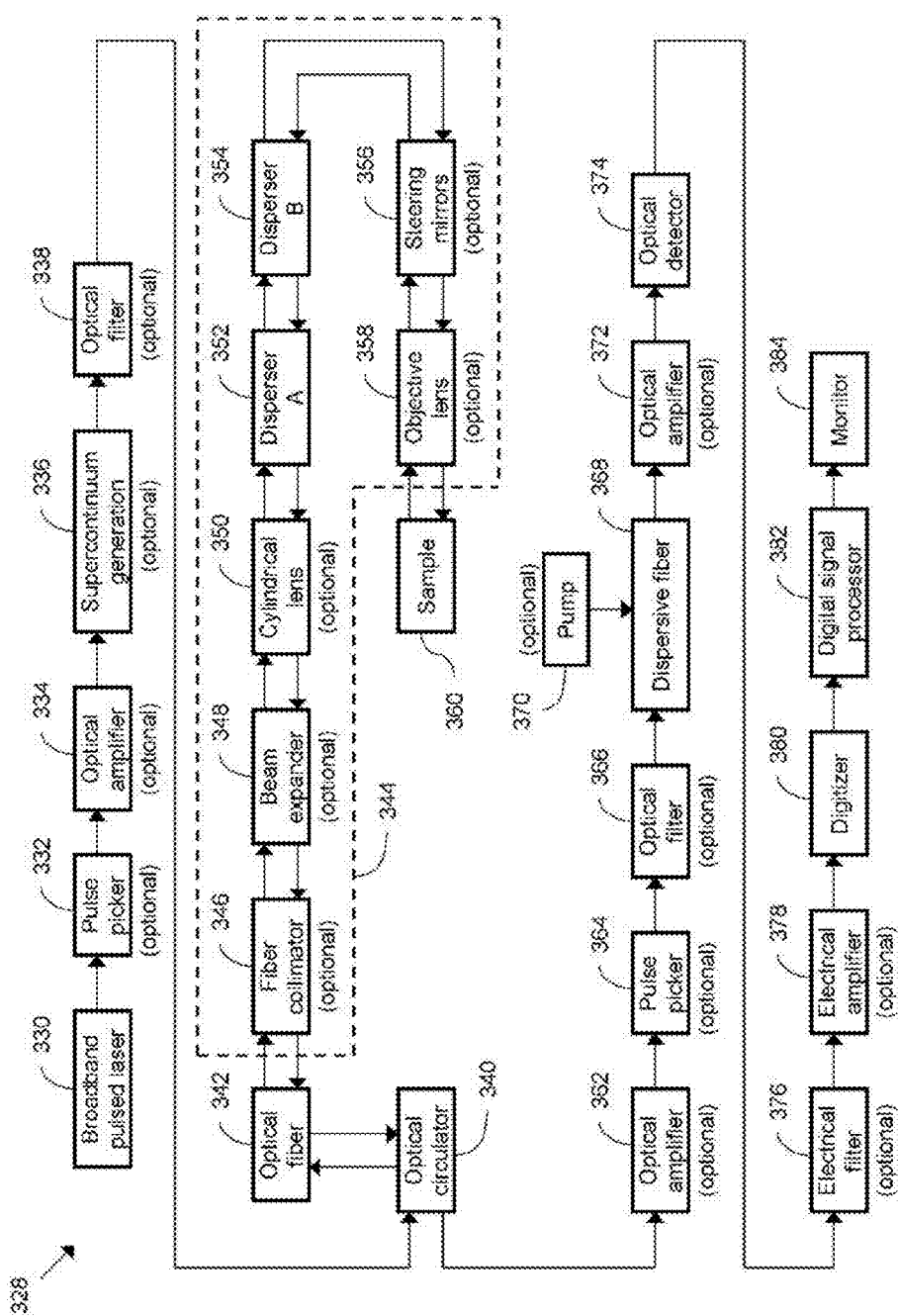
FIG. 10 is a schematic block diagram of an apparatus embodiment configured for optically amplified two-dimensional space-time endoscopy based on CWEETS using a broadband pulse laser.

The apparatus shown in FIG. 10, is basically equivalent to the apparatus 116 of FIG. 6 except that the probe optics including the optional fiber collimator 346, beam expander 348, cylindrical lens 350, disperser A 352, disperser B 354, steering mirrors 356, and objective lens 358 are miniaturized into an endoscopic probe 344. The broadband pulsed laser 330, and optional pulse picker 332, optical amplifier 334, supercontinuum generator 336 and optical filter 338 are the same.

The optical fiber 342 is used to guide the incident and back-reflected spectral brush to and from the miniaturized endoscopic probe 344. In practice, the micro-optical components can be assembled using refractive-index-matched epoxies, thereby reducing reflections from optical interfaces. The rest of the parts including the optical source 330 and detection system are identical to those in apparatus embodiment 116. Accordingly, the optical signal from the optical circulator 340 is optionally amplified and filtered with optical amplifier 362, pulse picker 364 and optical filter 366 and directed to the dispersive fiber 368 that is optionally pumped with pump 370. The dispersed signal may also be amplified by an optional amplifier 372 before detection by the optical detector 374. The resulting electrical signal may also be filtered and amplified by electrical filter 376 and electrical amplifier 378 and digitized with digitizer 380. The digital signal may be processed with processor 382 and observed with monitor 384 and stored.

Figure 11:
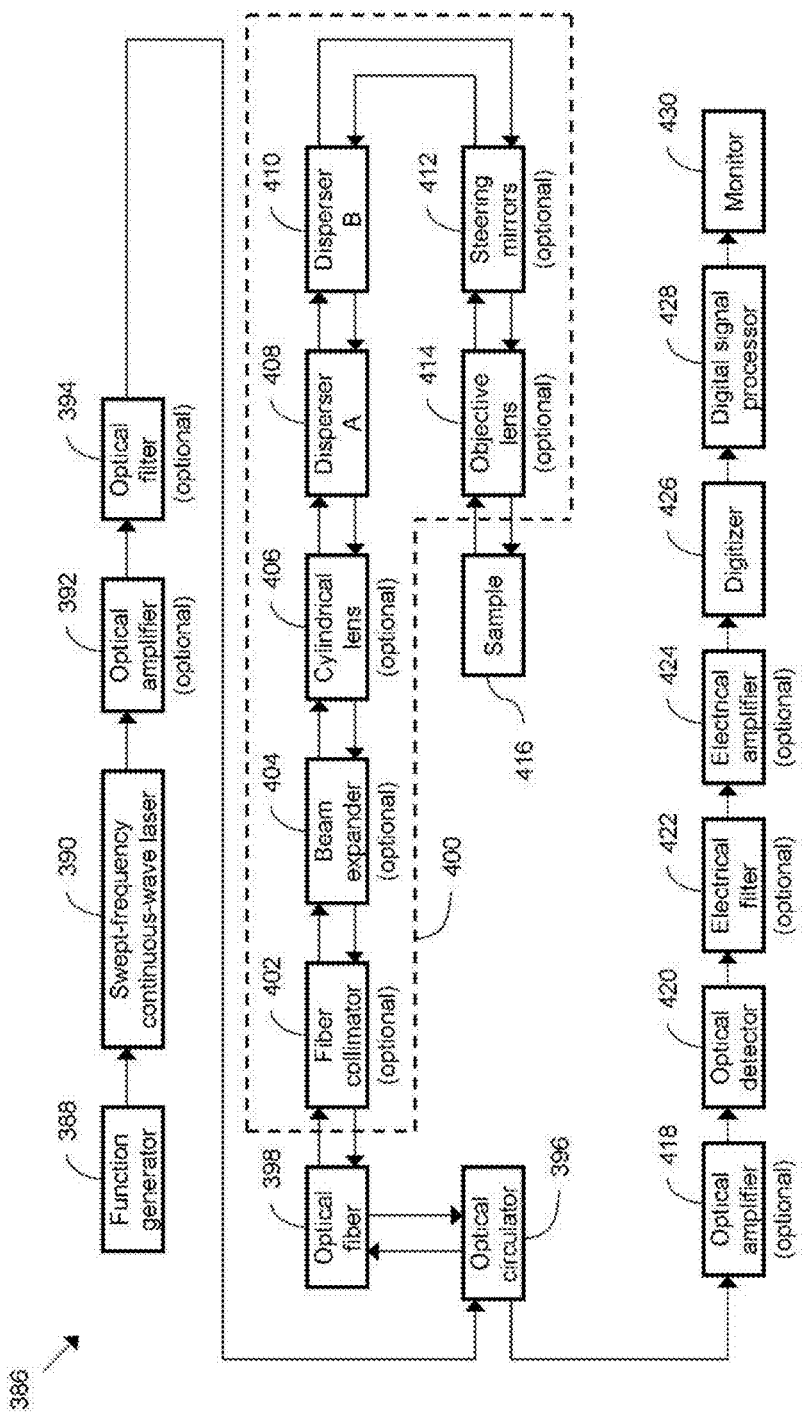
FIG. 11 is a schematic block diagram of an apparatus embodiment configured for optically amplified two-dimensional space-time endoscopy based on CWEETS using a swept-frequency continuous-wave laser.

Similarly, the apparatus 170 can be adapted for two-dimensional endoscopy using a swept frequency continuous wave laser light source. As seen in FIG. 11, an apparatus 386 configured for using Method 22 of FIG. 2 for endoscopy is generally shown. Apparatus 386 is essentially the same as apparatus 170 of FIG. 7 except that the probe optics including the optional fiber collimator 402, beam expander 404, cylindrical lens 406, disperser A 408, disperser B 410, steering mirrors 412, and objective lens 414 are miniaturized into an endoscopic probe 400. The functional generator 388, laser light source 390 and optional optical amplifier 392 and optical filter 394 are the same as described with apparatus 170.

The optical fiber 398 is used to guide the incident and back-reflected spectral brush to and from the miniaturized endoscopic probe 400. In practice, the micro-optical components are assembled using refractive-index-matched epoxies, thereby reducing reflections from optical interfaces. The rest of the parts including the optical source 390 and detection system are identical to those in apparatus 170. Accordingly, the optical amplifier 418, optical detector 420, electrical filter 422, electrical amplifier 424, digitizer 426, digital processor 428 and monitor 430 are the same as described in FIG. 7.

Figure 12:
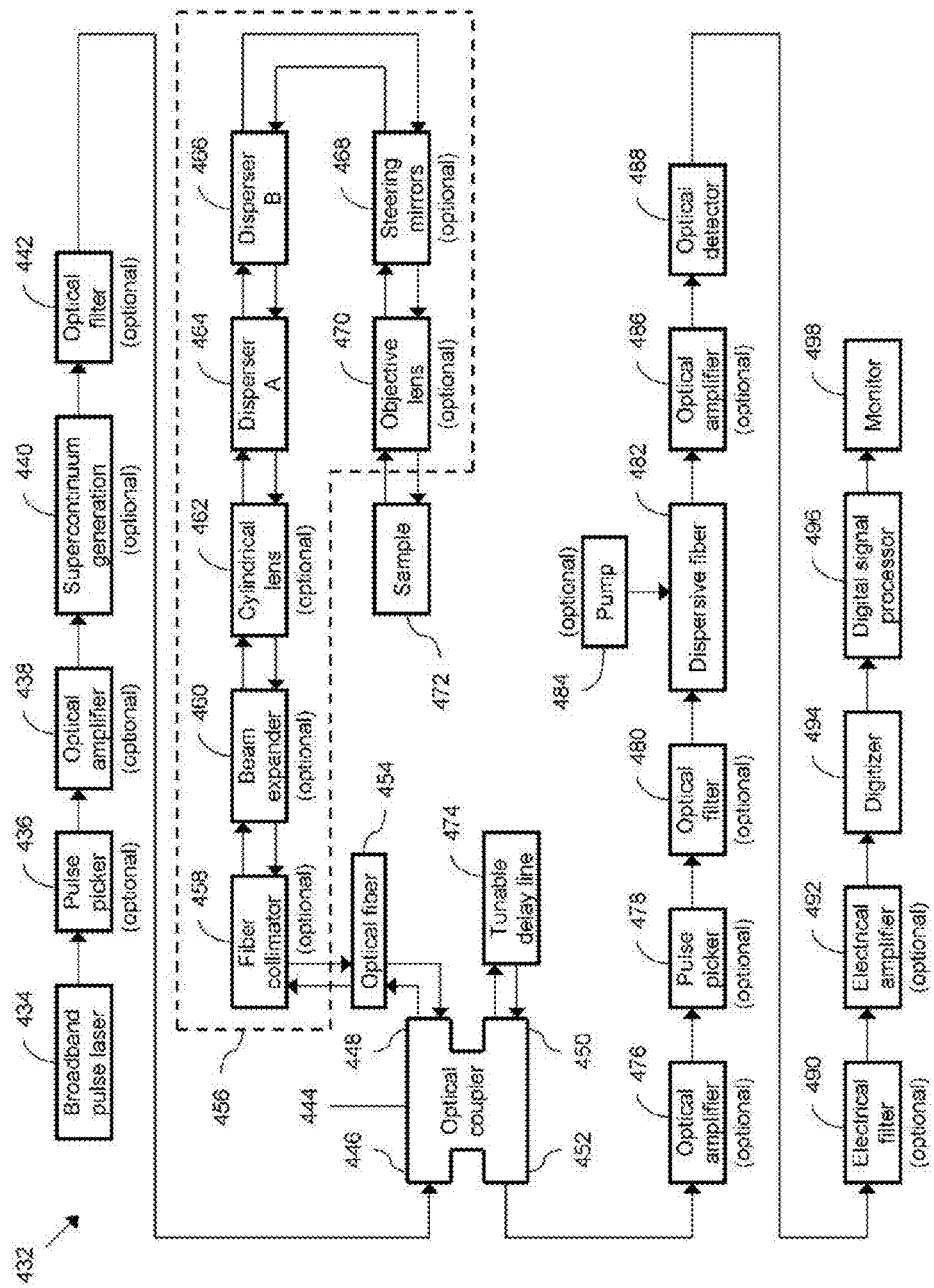
FIG. 12 is a schematic block diagram of an apparatus embodiment configured three-dimensional space-time endoscopy based on CWEETS using a broadband pulse laser in an interferometric configuration.
Figure 13:
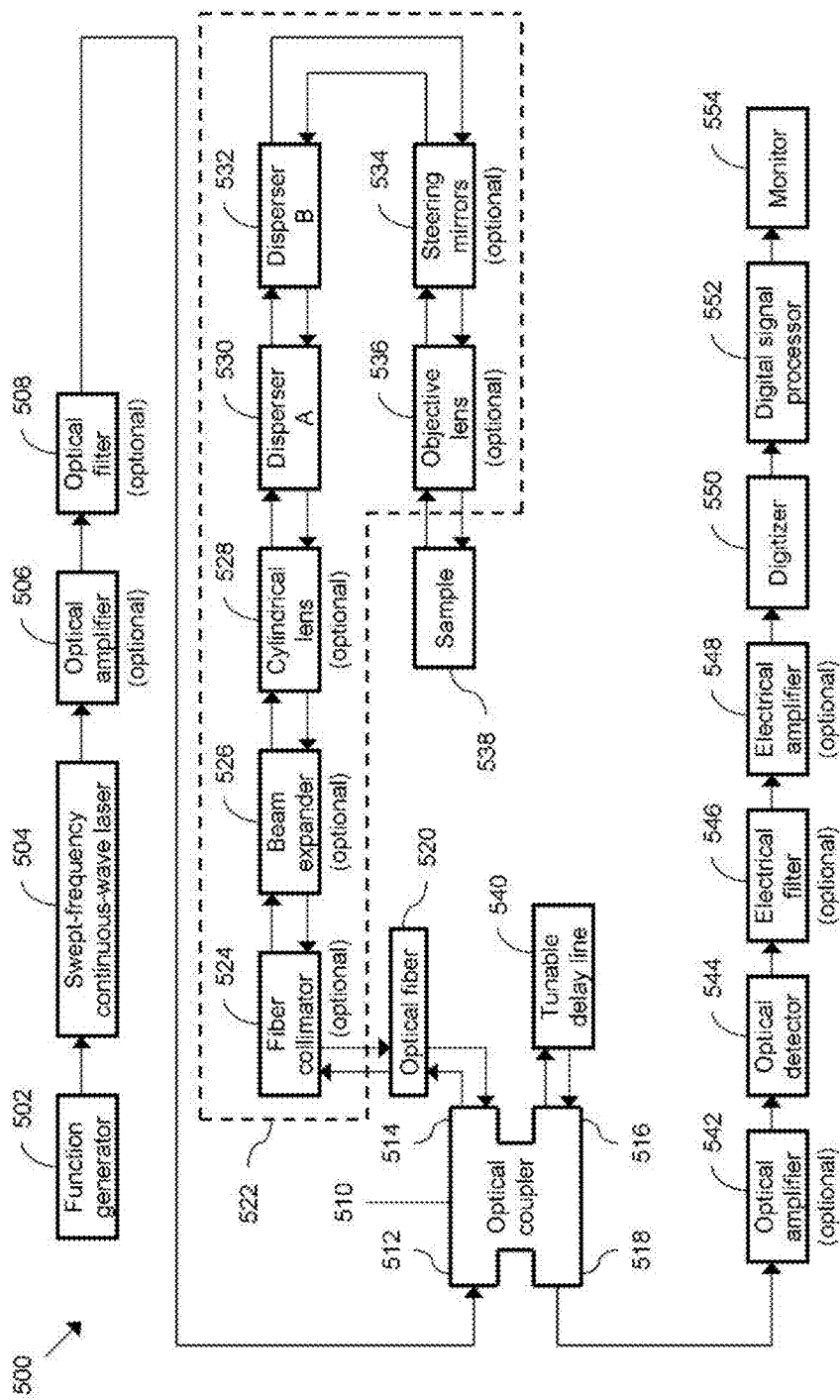
FIG. 13 is a schematic block diagram of an apparatus embodiment configured for three-dimensional space-time endoscopy based on CWEETS using a swept-frequency continuous-wave laser in an interferometric configuration.

The three dimensional methods and devices can also be adapted for use with endoscopy and other observational and diagnostic uses. FIG. 12 and FIG. 13 are exemplary schematic block diagrams of embodiments adapted for three-dimensional endoscopy that are extensions of the apparatus 212 of FIG. 8 and apparatus 276 of FIG. 9 respectively.

Referring now to FIG. 12, a schematic block diagram of one embodiment of an apparatus 432 configured to perform Method 32 of FIG. 3 adapted for endoscopy of sample 472 is shown. The apparatus 432 is basically the structural and functional equivalent of apparatus 212 discussed above, except that the probe optics including the optional fiber collimator 458, beam expander 460, cylindrical lens 462, disperser A 464, disperser B 466, steering mirrors 468, and objective lens 470 are miniaturized into an endoscopic probe 456. The light source assembly of broad band pulse laser 434, pulse picker 436, optical amplifier 438, supercontinuum generator 440, optical filter 442 and optical coupler 444 with ports 446, 448, 450, and 452 are the same as described with apparatus 212. Likewise, the image detection and processing assembly of optical amplifier 476, pulse picker 478, optical filter 480, pump 484, dispersive fiber 482, optical amplifier 486, optical detector 488, electrical filter 490, electrical amplifier 492, digitizer 494, digital signal processor 496 and monitor 498 are the same as their counterparts in apparatus 212.

The optical fiber 454 is used to guide the incident and back-reflected spectral brush to and from the miniaturized endoscopic probe 456. In practice, the micro-optical components are assembled using refractive-index-matched epoxies, thereby reducing reflections from optical interfaces.

Similarly FIG. 13, is a schematic block diagram of one embodiment of an apparatus 500 configured to use Method 44 of FIG. 4 for endoscopy of sample 528. The apparatus is structurally and functionally equivalent to the apparatus 276 in FIG. 9 except that the probe optics including the optional fiber collimator 524, beam expander 526, cylindrical lens 528, disperser A 530, disperser B 532, steering mirrors 534, and objective lens 536 are miniaturized into an endoscopic probe 522. The optical fiber 520 is used to guide the incident and back-reflected spectral brush to and from the miniaturized endoscopic probe 522. In practice, the micro-optical components are assembled using refractive-index-matched epoxies, thereby reducing reflections from optical interfaces.

The rest of the parts including the optical source 504, function generator 502, optical amplifier 506, optical filter 508 and detection system including the optical coupler 510 with ports 512, 514, 516 and 518, and optical amplifier 542, optical detector 544, electrical filter 546, electrical amplifier 548, digitizer 550, digital signal processor, and monitor 554 are structurally and functionally identical to those described in the apparatus 276 embodiment.

Figure 14:
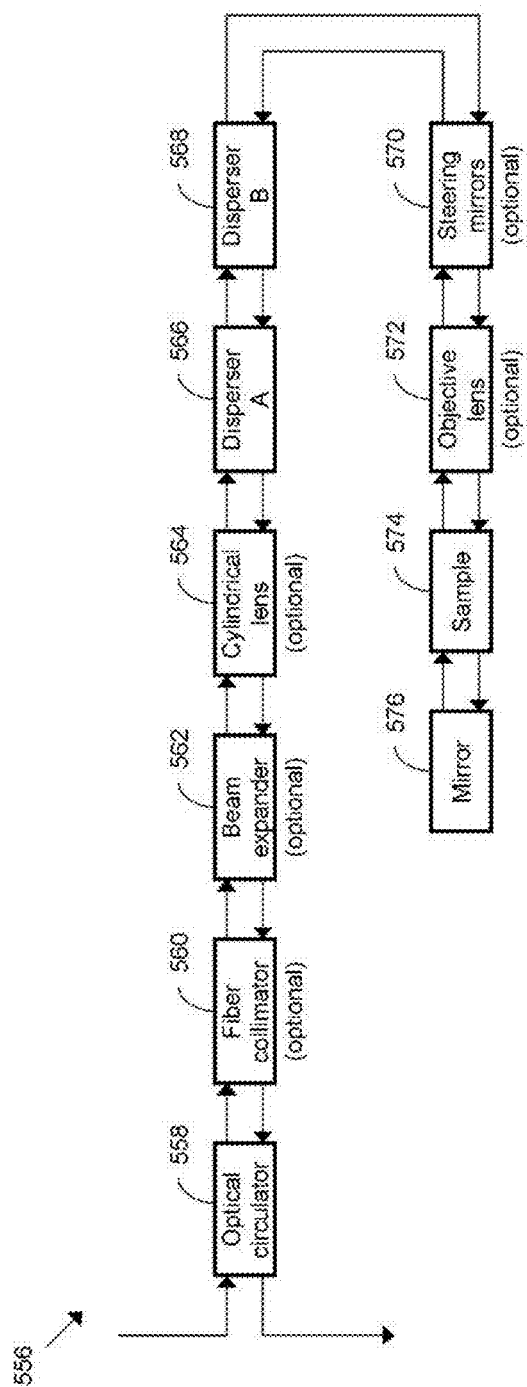
FIG. 14 is a schematic block diagram of one embodiment of space-time imaging based on measuring the transmitted spectral brush through the sample using a mirror placed at the back of the sample.

The devices and methods shown in FIGS. 1-13 use spectral encoding of the back reflection of an optical beam directed to a sample by spatial dispersion. However, alternative measurements may be used. For example, FIG. 14, is a schematic block diagram of one embodiment an apparatus 556 that measures the transmitted spectral brush through the sample instead of the back-reflected spectral brush. The optical beam is directed through the optical circulator 558 and the optional fiber collimator 560, beam expander 562 and cylindrical lens 564 to disperser A 566 and disperser B 568. The brush from the dispersers is directed to the sample by optional steering mirror 570 and objective lens 572.

In this embodiment, the transmitted spectral brush emerging through the sample 574 returns to the sample 574 by the mirror 576 placed at the back of the sample 574 and is directed toward the optical circulator 558. As a result, the doubly transmitted spectral brush returns to the dispersers 566 and 568. The other blocks in this method are basically equivalent to those in the apparatus of FIG. 6 or FIG. 7.

Figure 15:
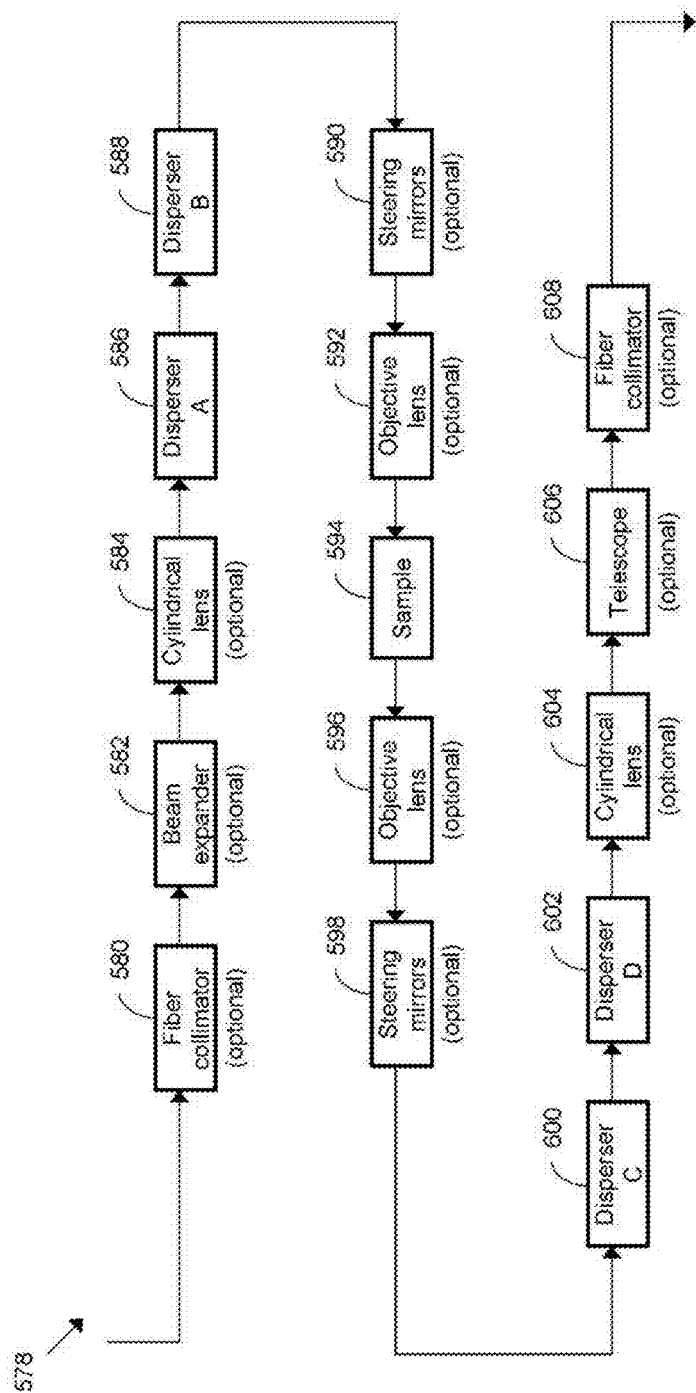
FIG. 15 is a schematic block diagram of one embodiment of space-time imaging based on measuring the transmitted spectral brush using another pair of spatial dispersers.

Alternatively, space-time imaging can be done based on measuring the spectral brush using a second pair of spatial dispersers. A schematic block diagram of another embodiment of an apparatus 578 that measures the transmitted spectral brush through the sample is shown in FIG. 15. In this embodiment, an identical pair of dispersers (disperser C 600 and disperser D 602) to disperser B 588 and disperser A 586, respectively are placed at the transmission of the spectral brush through the sample 594, and the spectrally encoded spatial information of the sample 594 is decoded using the transmission optics instead of using an optical circulator which is used in the reflection measurement employed in the other methods discussed in the present invention. The beam is transmitted through optional fiber collimator 580, beam expander 582 and cylindrical lens 584 to disperser A 586 and disperser B 588. The dispersed beam is directed to the sample 594 through optional steering mirror 590 and objective lens 592. The transmission of the brush through the sample 594 is directed through optional objective lens 596 and steering mirrors 598 to the second set of dispersers, disperser C and disperser D, optional cylindrical lens 604, telescope 606 and fiber collimator 608.

This alternative apparatus and method may be useful for observation of biological tissue or cells which tend to have low reflectance that makes it relatively difficult to probe biological samples with reasonable imaging sensitivity. The optical source and detection system in this method are equivalent to those employed in the other methods, depending on the application.

The use of a laser as a light source for two-dimensional spectral brush permits real time images of the sample. The use of a laser may also permit the application of high intensity laser light to the sample as well. For example, the invention may be adapted for use as an endoscope, as shown in FIGS. 10-13, that may also have the ability to direct high intensity laser light to the sample. One embodiment of a two or three-dimensional spectrally encoded endoscopic imaging apparatus 610 combined with laser ablation is shown schematically in FIG. 16.

Figure 16:
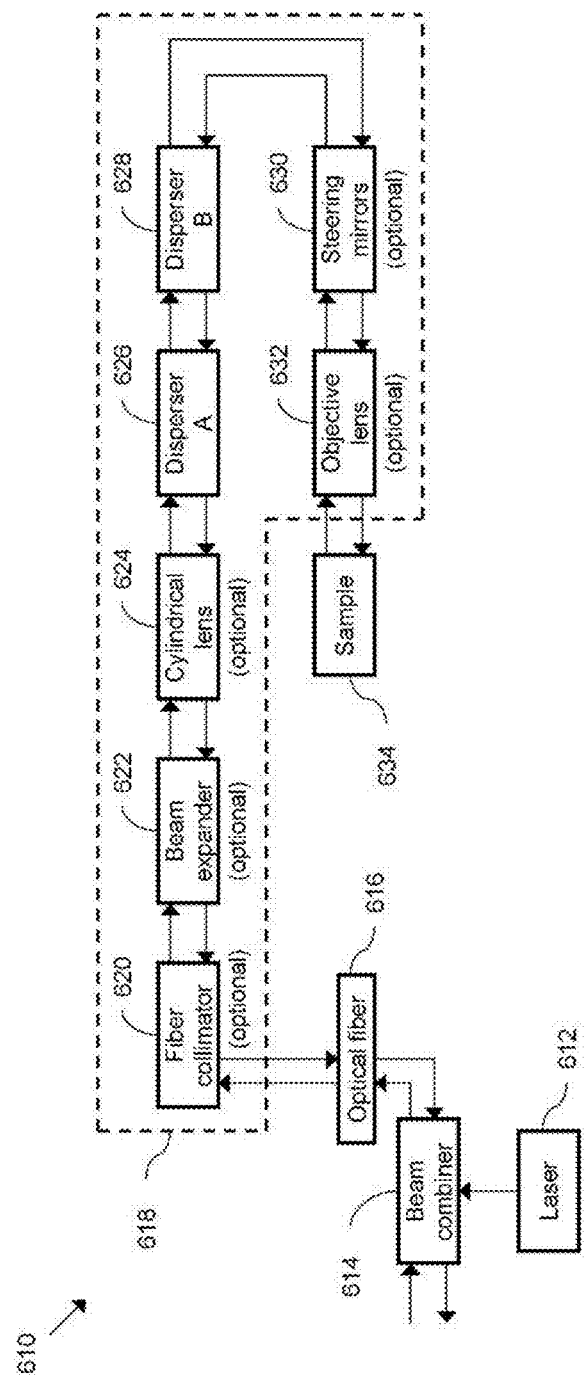
FIG. 16 is a schematic block diagram of one embodiment of two or three-dimensional space-time imaging combined with laser ablation.

In the embodiment of the apparatus 610 shown in FIG. 16, the laser 612 may be a powerful continuous-wave or pulse laser is combined with the endoscopic probe laser via the beam combiner 614, which may be a fiber coupler or beam splitter. The endoscope imaging probe 618 that is shown in FIG. 16 is the same embodiment shown in FIGS. 10-14 to illustrate the principle but other configurations may be used. The probe has an optional fiber collimator 620, beam expander 622 and cylindrical lens 624 to process the beam before the dispersers. Disperser A 626 and disperser B 628 preferably provided a course and fine spectral brush to sample 634 through optional steering mirror 630 and objective lens 632.

A second laser 612 can be used to heat or ablate a targeted area of the sample 634 while monitoring the sample 634 with the probe laser which may be a broadband pulse laser or swept-frequency continuous-wave laser. This apparatus 612 does not require any mechanical scanning within the probe and is therefore ideal for compact, mechanical noiseless endoscopy and laser surgery.

Variations in the detection portion of the apparatus and methods may also be desirable in specific adaptations of the invention. For example, detection may be improved with correlation matching against a database in the time domain or the spatial domain.

Figure 17:
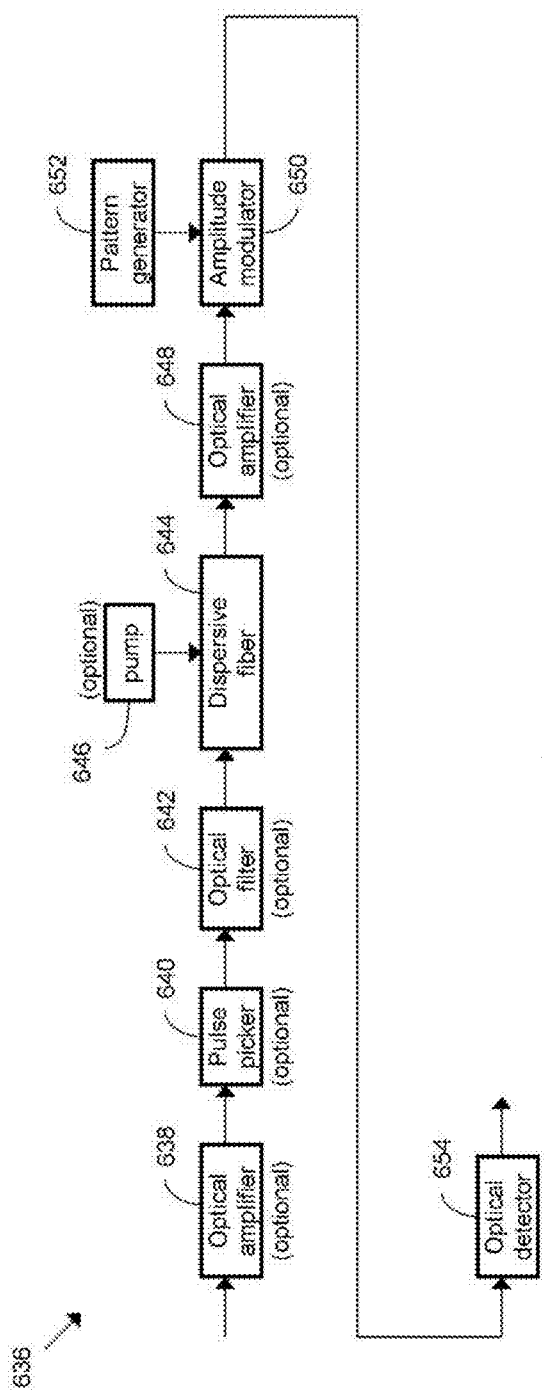
FIG. 17 is a schematic block diagram of space-time imaging with optical correlation matched detection against a database in time domain.

Referring now to FIG. 17, a schematic block diagram of one embodiment of an apparatus 636 for two or three-dimensional spectrally encoded imaging with optical correlation matched detection of measured images with a large image database in the time domain is shown. In this illustration, the optical source and detection systems may be identical to those in shown in apparatus 116 in FIG. 6 with the addition of a pattern generator 652 and amplitude modulator 650 between the optional amplifier 648 and the optical detector 654. The beam from the optical circulator may be processed with the optional optical amplifier 638, pulse picker 640 and optical filter 642 before the dispersive fiber 644.

The amplitude of the temporal waveform from the dispersive fiber 644 (which may be optically pumped by the pump 646) is modulated by the amplitude modulator 650, which is driven by the pattern generator 652. Since the acquired image is in the form of serial data, optical correlation matched detection using the amplitude modulator 650 and pattern generator 652 can be done easily. Alternatively, the optical source can be a swept-frequency continuous-wave laser instead of using the dispersive fiber 644 and a broadband pulse laser.

Correlation matching against a database in the spatial domain can be illustrated in the apparatus 656 shown in the schematic block diagram of one embodiment of a two or three-dimensional spectrally encoded imaging with optical correlation matched detection of measured images with a large image database in the spatial domain using the transmission configuration of the invention shown in FIG. 15. In this illustration, the optical source and detection system may be identical to those in apparatus 116 of FIG. 6 with the addition of a 1-bit quantizer 704.

Accordingly, the apparatus 656 has the optional fiber collimator 658, beam expander 660, cylindrical lens 662, disperser A, 664, disperser B 666, steering mirrors 668 and objective lens 670 to direct a spectral brush to sample 672 as described previously. In this embodiment, the transmissions from sample 672 are received by optional objective lens 674, steering mirrors 676, spatial light modulator 678 to disperser C 680 and disperser D 682. The results of disperser C 680 and disperser D 682 are preferably directed through optional cylindrical lens 684, telescope 686, fiber collimator 688, optical amplifier 690, pulse picker 692 and optical filter 694 to the dispersive fiber 696. The dispersive fiber may be optionally pumped by pump 698 and amplified by optical amplifier 700 and detected with optical detector 702 and subject to 1-bit quantizer 704. The electrical signal may be filtered, amplified and digitized with optional electrical filter 706, electrical amplifier 708 and digitizer 710. The digitized signal is processed with digital signal processor 712 and viewed on monitor 714 and stored.

Figure 18:
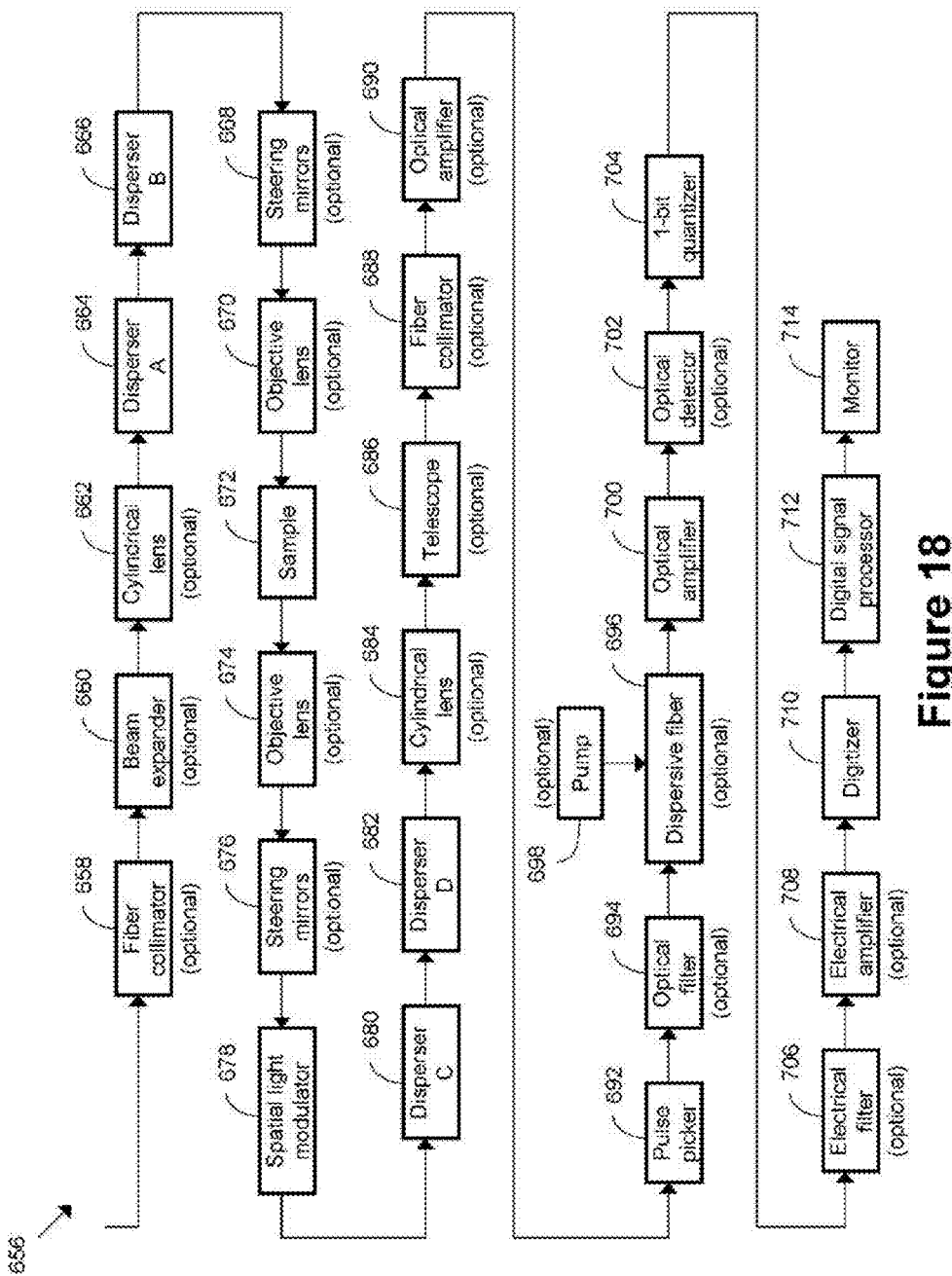
FIG. 18 is a schematic block diagram of space-time imaging with optical correlation matched detection against a database in spatial domain.

Before the sample image-encoded spectrum is transformed back into the time domain, the spatial light modulator 678 can be used to modulate the image-encoded spectrum in the spatial domain in the embodiment shown in FIG. 18. The modulated spectrum is then directed toward the fiber collimator 688 via the disperser C 680 and disperser D 682 and detected by the optical detector 702. The detected signal is subject to the 1-bit quantizer 704 for analog matched detection. Alternatively, the optical source can be a swept-frequency continuous-wave laser instead of using the dispersive fiber 696 and a broadband pulse laser.

With regard to the high-speed real-time image acquisition by the serial time encoded amplified imaging (STEAD described in the apparatus embodiments 116, 212, 328, and 432, it has been observed that a higher imaging frame rate can be achieved, but at the expense of the number of image pixels, or vice versa. This can be understood by the fact that the maximum number of pixels acquired by STEAI is ultimately determined by the ratio of the repetition time interval of the pulse laser to the shortest sampling time of the digitizer. That is, the higher the frame rate (shorter pulse interval), the smaller the number of pixels that can be accommodated. Nevertheless, this trade-off can be overcome by using a "time-gating" technique based on wavelength division multiplexing different spectral bands in the spectral brush, for example. Other techniques may also be used.

Figure 19:
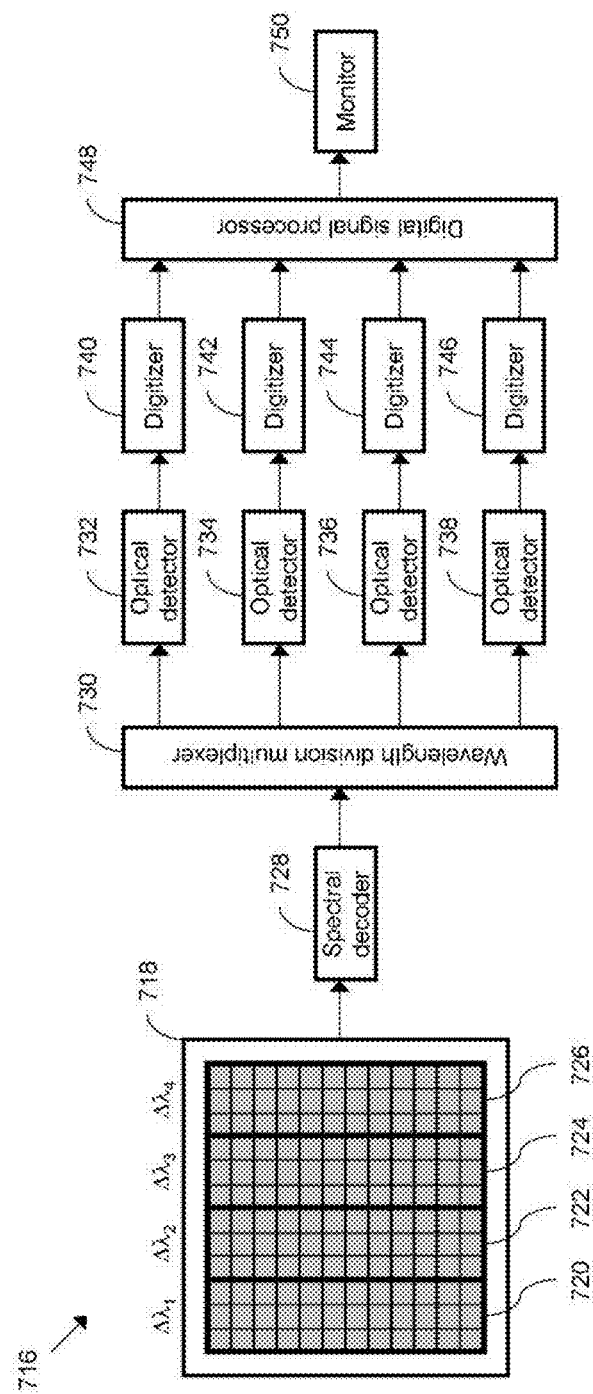
FIG. 19 is a schematic block diagram of the time-gating technique to overcome the trade-off between the number of image pixels and the image frame rate in the STEAI technique.

In FIG. 19, a schematic block diagram of one time-gating technique to overcome the trade-off between the number of image pixels and the frame rate is shown in the apparatus 716. This approach is applicable to embodiments 116, 212, 328, and 432 described previously.

The encoded spectral brush 718 is fed to into the spectral decoder 728 which performs a dispersive Fourier transform to decode the spectrum into the temporal waveform. The wavelength division multiplexer 730 then multiplexes the spectral bands 720 through 726 (from the spectral brush 718) of the signal into four separate arms in this illustration. Each multiplexed spectral band is then detected by the optical detectors 732 through 738 and digitized by the digitizers 740 through 746 separately. Because the spectrum is already mapped into the time domain by the spectral decoder 728 beforehand, the wavelength multiplexer 730 essentially performs time-gating of the signal.

While FIG. 19 illustrates a 1-to-4 multiplexer as an example, a 1-to-N multiplexer can be implemented in practice. It thus increases the number of the pixels of a factor of N without sacrificing the image frame rate or increases the frame rate of a factor of N given a fixed number of image pixels.

It is realized that the performance of the parallel channel digitizers shown in FIG. 19 may be limited by the mismatches between different channels. Interchannel gain, offset, and clock skew create spurious tones in the frequency domain and limit the dynamic range. The problem can be eliminated by calibrating the whole system with a known sample for imaging, which corrects the interchannel mismatch errors.

Embodiments of the present invention are described with reference to flowchart illustrations of methods and systems according to different embodiments of the invention. These methods and systems can also be implemented as computer program products. In this regard, each block or step of a flowchart, and combinations of blocks (and/or steps) in a flowchart, can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts support combinations of means for performing the specified functions, combinations of steps for performing the specified functions, and computer program instructions, such as embodied in computer-readable program code logic means, for performing the specified functions. It will also be understood that each block of the flowchart illustrations, and combinations of blocks in the flowchart illustrations, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s).

The invention may be better understood with reference to the accompanying examples, which are intended for purposes of illustration only and should not be construed as in any sense limiting the scope of the present invention as defined in the claims appended hereto.

Example 1

In order to demonstrate the functionality of the invention, the embodiment of the apparatus 116 shown schematically in FIG. 6 was constructed and tested using method shown in FIG. 1. The optical source that was used was a broadband pulse laser with a center wavelength and bandwidth of 1587 nm and 15 nm, respectively. The average optical power and pulse repetition rate of the laser was about 20 mW and 36.7 MHz, respectively. By pulse-picking the pulse train, the pulse repetition rate was reduced down to 6.1 MHz which is equivalent to a pulse interval of 163 ns. The spectrum of the laser was broadened by a high nonlinearity fiber to generate large bandwidth.

The combination of the virtually-imaged phased array (VIPA) with a free spectral range (FSR) of 67 GHz and a linewidth of 550 MHz and the diffraction grating with a groove density of 1200 lines/mm formed two-dimensional spectral brushes which are incident onto the sample. The average optical power of the spectral brush probe is about 2 mW. The spatial information of the sample was encoded into the spectrum of the back-reflected two-dimensional brushes from the sample, which were directed toward the spectrum decoder via dispersers and the optical circulator.

The fiber coupler acted as an iris for confocal microscopy. The signal was pre-amplified and filtered by an L-band erbium-doped fiber amplifier (EDFA) with a gain bandwidth of 50 nm centered at 1590 nm and a band-pass filter, respectively, and then was mapped into a temporal waveform by the Raman-amplified dispersive Fourier transformer that consisted of four continuous-wave Raman pumps with wavelengths of 1470 nm, double 1480 nm, and 1490 nm and about 200 mW per Raman pump, wavelength-division multiplexers (WDMs), and dispersion compensation fiber (DCF) with a total group-velocity dispersion of −3.3 ns/nm.

The temporal waveform was captured by a single photodiode and digitized by a high-speed digital oscilloscope with a bandwidth of 16 GHz and a sampling rate of 50 GS/s. The final image was retrieved by digital image processing with a computer and software programming.

The number of image pixels observed was found to be about 2500 based on the bandwidth of the probe laser, the sampling rate of the oscilloscope, and the FSR of the VIPA. In this demonstration, the bandwidth of the gain bandwidth of the Raman amplifier (~15 nm) limited the number of image pixels. However, this was not an inherent limitation of the technique. The use of additional Raman pumps at different wavelengths can significantly increase the optical bandwidth, and hence, the number of pixels. The shutter time duration was found to be about 270 ps based on the dispersion in the spatial dispersers and is expected to be much shorter if dispersion compensation (e.g. by use of a pair of prisms) is implemented before the dispersers. The net image amplification factor of the optical image amplifier system is found to be 25 dB which results from the sum of the EDFA gain of 20 dB, the DCF loss of 20 dB, the Raman gain of 35 dB, and the propagation loss of 10 dB.

In digital image processing, the captured waveform was first digitally band-passed filtered to remove high frequency noise, DC component, and the slow-varying envelope of the waveform. The filtered waveform was normalized by the filtered background waveform which corresponds to the background image. This normalization step eliminates the fringe pattern resulting from the spectral brush. Then, the normalized waveform was digitally carved into a number of segments, which were equivalent to the columns of pixels in the final image. This carving step is done based on the knowledge of the FSR of the VIPA, which corresponds to the column length of the final image. The third-order dispersion (which results in nonlinear frequency-to-time mapping) was also included in this step to avoid the skewing problem in the image reconstruction. The resultant image quality was further enhanced by noise removal using the Wiener filter, image interpolation and contrast equalization.

The basic performance of the imaging technique was evaluated. The amplified dispersive Fourier-transformed pulse train with a pulse interval of 163 ns measured by the photodetector and displayed on the oscilloscope showed that each pulse contains a snapshot of the spatial information of the sample which is encoded into its spectrum. The imaging frame rate of more than 6 Mfps was clearly evident. The consistency between the temporal waveform (single pulse) displayed by the oscilloscope and the spectrum measured by a conventional optical spectrum analyzer validated the frequency-to-time mapping operation by dispersive Fourier transformation. Incorporating the Raman amplification within the DCF was found to be significant. The optical image amplifier raised the otherwise undetectable weak signal well above the detector noise floor, overcoming the trade-off between imaging sensitivity and scan rate.

To show the image quality of the imaging technique which we call serial time-encoded amplified imaging (STEAD, the snapshots of a few test samples captured only within 70 ns were compared with the images obtained by a CCD placed at the back of the sample, proving the imaging functionality of the embodiment in FIG. 6.

Example 2

A microfluidics experiment to attempt to observe ultrafast motion was conducted with the apparatus. In recent years, microfluidics has revolutionized molecular biology procedures for enzymatic analysis, proteomics, and DNA analysis based on polymerase chain reaction on microfluidic biochips.

The optical source that was used was a mode-locked femtosecond laser. The center wavelength, bandwidth, pulse energy and pulse-repetition rate of the laser after spectral broadening, filtering and pulse picking were 1,590 nm, 15 nm, 82 pJ and 6.1 MHz, respectively. The 2D spectral pattern was produced by the 2D spatial disperser and focused onto the sample using an objective lens.

The 2D disperser was a pair of orthogonally oriented dispersers, which consisted of a diffraction grating with a groove density of 1,200 lines per millimeter and a virtually imaged phased array with a free spectral range of 67 GHz and a linewidth of 550 MHz. The amplified dispersive Fourier transformer consisted of a DCF with a total group-velocity dispersion of 23.3 ns/nm and four ~300-mW continuous-wave pump lasers at 1,470-1,490 nm (chosen to produce a uniform Raman gain profile across the optical fiber bandwidth with ~1-dB variation) and wavelength-division multiplexers that coupled the pump lasers into and out of the DCF. The digitizer had a bandwidth of 16 GHz and a sampling rate of 531010 samples per second. The captured 1D temporal data was sorted into a 2D matrix in the digital domain for image reconstruction.

An ultrafast microfluidic laminar flow of water-suspended metal microspheres in a hollow fiber was captured by the imaging technique with the temporal resolution of 163 ns. The microfluidic system consists of a 15 cm long hollow fiber with an inner diameter of 50 µm. The metal microspheres were suspended in water with a small amount of ethanol (for wetting the metal microspheres). The flow of metal microspheres with diameters of 10-30 µm at a flow speed of about 2.4 m/s in the hollow fiber with a diameter of 50 µm from the right to the left were observed. This was the first time that a fluidic system was observed in real time with such a fine temporal resolution. This demonstration promises an effective tool for imaging turbulent fluidic systems as well.

Example 3

To show the nanosecond time-resolved real-time imaging capability of the invention, the dynamical process of a laser-induced surface change in combination with laser ablation was monitored with the imaging technique and the apparatus illustrated in FIG. 16. Laser ablation is a powerful tool that has been used for many applications including laser surgery, laser cutting, laser engraving, and laser-induced breakdown spectroscopy.

In this example, a mid-infrared excitation pulse laser (with a pulse energy of 6 mJ and a pulse width of 5 ns) was focused at an angle onto the sample with a bilayer of aluminum and silicon dioxide deposited on top of a silicon-on-insulator substrate, while the two-dimensional spectral brushes are normal and incident onto the surface of the sample. The excitation pulse for the laser ablation was an optical parametric oscillator pumped by a Nd:YAG Q-switched laser. It generates a high power pulse with a center wavelength of 2.8 µm. A lens with a focal length of 75 mm produces a focused pulse with a fluence of about 20 J/cm$^2$ at the surface of the sample.

The back-reflected spectral brushes are subject to amplified dispersive Fourier transformation. Real-time snapshot sequences of the images captured by the detector with the temporal resolution of 163 ns (equivalent to the frame rate of 6.1 Mfps) were observed. The gradual change of the surface reflectivity due to the laser-induced mass ejection was evident. Further analysis of the time-sequenced surface reflectivity change also shows the time-delay between the pulse excitation and the sudden decrease in the surface reflectivity which correlates with the mass ejection process.

This observed phenomenon was a clear signature of the phase-explosion effect that occurred to the sample. Also scanning electron microscope image and depth profile of the sample, indicating that the excitation pulse ablated the aluminum and silicon dioxide layers and exposed the underneath silicon layer were taken. This was the first time that the phase-explosion effect was observed in real time without a pump-probe configuration. This demonstration firmly establishes the feasibility of monitoring laser-induced ultrafast transient processes such as laser surgery and laser cutting, using the imaging according to the invention.

Example 4

To illustrate a swept-frequency continuous wave light source embodiment of the invention, the apparatus shown schematically in FIG. 7 was constructed. The apparatus encoded the spatial information of a sample into the intensity of a swept-frequency continuous-wave laser in a two-dimensional spectral brush scanning pattern.

The optical source was a tunable-wavelength continuous-wave laser. The frequency of the laser could be tuned from 1520 nm to 1570 nm continuously without mode-hopping. The average optical power was about 10 mW. The combination of the virtually-imaged phased array (VIPA) with a free spectral range (FSR) of 67 GHz and a linewidth of 550 MHz and the diffraction grating with a groove density of 1200 lines/mm formed a two-dimensional spectral brush pattern. The average optical power of the spectral brush probe was about 2 mW. The sample was a calibration target often used for imaging experiments.

When the laser frequency was chirped by the external function generator, the laser with the increasing or decreasing frequency made a raster scan on the sample. The driving function of the function generator was used to calibrate the location of the laser on the sample to construct an image of the sample in digital image processing. The sweep speed was limited to ~1 Hz due to the specifications of the laser. However, the sweep speed could be significantly increased to 100 kHz by use of a high-speed swept-source laser (e.g. a swept-source laser for optical coherence tomography). In this example, optical image amplification was not used since the laser had a relatively high power and the scan speed was relatively slow, allowing the photodetector to capture a sufficient number of photons. However, optical image amplification can be implemented in this system to increase the imaging sensitivity.

In digital image processing, the captured waveform was first digitally band-passed filtered to remove high frequency noise and the slow-varying envelope of the waveform. The filtered waveform was normalized by the filtered background waveform which corresponded to the background image. This normalization step eliminated the fringe pattern resulting from the spectral brush. Then, the normalized waveform was digitally carved into a number of segments, which were equivalent to the columns of pixels in the final image. This carving step was done based on the knowledge of the FSR of the VIPA and corresponded to the column length of the final image. The resultant image quality was further enhanced by noise removal using the Wiener filter, image interpolation and contrast equalization.

The acquired image of the sample had some distortion. However, the image distortion that was present in the figure can be removed by compensating for the nonlinear raster scan of the swept-frequency laser. This proof-of-principle demonstration established the imaging functionality of the embodiment shown in FIG. 7.

Example 5

To further illustrate the invention, the embodiment shown schematically in FIG. 7 and FIG. 16 was constructed. The optical source was a combination of an incoherent light source (for imaging) and a frequency-tunable laser (for laser ablation or surgery) along the same fiber that eliminates the need for mechanical scanning.

In this example, an incoherent broadband light source (an amplified spontaneous emission source with a center wavelength of 1543 nm and bandwidth of 17 nm) was used to deliver the light (approximately 2 mW) via a singlemode fiber, a 2D spatial disperser, and an objective lens (a focal length of f=4.5 mm) to the sample. The 2D spatial disperser consisted of a pair of spatial dispersers, a diffraction grating (a groove density of 1200 lines/mm), and a virtually imaged phased array (VIPA) (a thickness of 1.5 mm) that is essentially a tilted Fabry-Pérot cavity. The combination of the virtually-imaged phased array (VIPA) with a free spectral range (FSR) of 67 GHz and a linewidth of 550 MHz and the diffraction grating with a groove density of 1200 lines/mm forms a two-dimensional spectral brush pattern.

To demonstrate the capability of simultaneous imaging and laser surgery with the spectral brush pattern, a test sample was first imaged. A collimated broadband beam (~1 mm) was focused by a cylindrical lens (a focal length of 200 mm) onto the front side of the VIPA (a tilted angle of θVIPA=~2.5°) and a refractive index of n=1.48) through the uncoated window area. The reflectivity of the coated area on the front and back surface are 99.9% and 95%, respectively. The spectral beam has a beam diameter of ~2 mm, which almost fills the back aperture of the objective lens. The image that is now encoded into the spectrum of the back-reflected spectral beam was then directed through the same 2D spatial disperser, after which it reentered the single mode fiber and was routed, via an optical circulator, to an optical spectrum analyzer (OSA) that captured the image-encoded spectrum. The imaging sensitivity can be enhanced by optical amplification of the image-encoded spectrum using optical fiber amplifiers.

A continuous wave external-cavity frequency tunable diode laser (1520 nm-1570 nm) and an erbium-doped fiber amplifier (EDFA) were added to the apparatus via a fiber combiner to perform laser ablation and to image the process in real time. The ablation laser power was ~300 mW.

The experiment was performed on a bovine tissue sample. The laser surgery was performed by tuning the frequency of the frequency-tunable laser without the need for mechanical scanning. Here both imaging and laser surgery were done without moving any mechanical components. Since the ablation laser was coupled into the same 2D disperser that performs the imaging, it follows the same wavelength-to-spatial-coordinate mapping as the spectral shower that performs the imaging. By tuning the wavelength of the laser, the ablation beam can be directed to any arbitrary position on the tissue without any mechanical movement of the probe or the tissue. Hence high-precision microsurgery can be performed by computer-controlled tuning of the laser wavelength according to a preprogrammed pattern.

This example illustrates the capability of this instrument to perform in situ high-precision laser microsurgery and simultaneously monitor the process with the same single fiber probe. This capability bodes well for microsurgery applications that require higher precision than what is achievable with manual manipulation of the surgical probe.

From the foregoing it can be seen that the present invention can be embodied in various ways, including, but not limited to, the following:

1. A method of optical imaging, comprising: generating a two-dimensional spectral brush with a two-dimensional disperser and a light source; exposing a sample to said two-dimensional spectral brush; encoding spatial information of the sample into the spectrum of the spectral brush to provide a back reflected spectral brush; decoding the back reflected spectral brush to provide an electric signal; and processing the electric signal to retrieve a two-dimensional image.

2. A method according to embodiment 1, wherein said light source is selected from group of light sources consisting essentially of an incoherent light source, a broadband pulse laser light source and a swept frequency continuous-wave laser light source.

3. A method according to embodiment 1, further comprising refining a broadband pulse laser light source beam with a pulse picker, an optical amplifier, a supercontinuum generator, an optical filter, a fiber collimator, a beam expander and a cylindrical lens; and directing the refined light beam on the disperser to provide a two-dimensional spectral brush.

4. A method according to embodiment 1, further comprising refining a swept frequency continuous-wave laser light source beam with a function generator, an optical amplifier, an optical filter, a fiber collimator, a beam expander and a cylindrical lens; and directing the refined light beam on said disperser to provide a two-dimensional spectral brush.

5. A method according to embodiment 1, further comprising controlling the exposure of the sample with a spectral brush directed from the disperser through steering mirrors and an objective lens.

6. A method according to embodiment 1, wherein a two-dimensional spectral brush is generated by at least one orthogonally oriented coarse disperser and one fine disperser.

7. A method according to embodiment 6, where the coarse disperser comprises a diffraction grating and the fine disperser comprises a virtually imaged phased array.

8. A method according to embodiment 1, wherein the decoding comprises performing a Dispersive Fourier Transformation on broadband laser pulses to provide temporal waveform; capturing the waveform; digitizing the captured waveform to provide a digital signal; and processing the digital signal to produce an image.

9. A method according to embodiment 1, where the decoding comprises amplifying an encoded optical signal with an optical amplifier from continuous wave laser pulses to provide temporal waveform; detecting the optical signal to produce an electrical signal; improving the electrical signal with an electrical filter and an electrical amplifier; digitizing the improved electric signal to provide a digital signal; and processing the digital signal to produce an image.

10. A method according to embodiment 1, where the decoding comprises refining the encoded back reflected brush from a broadband laser light source with an optical amplifier, a pulse picker and an optical filter to produce a refined optical signal; directing the optical signal through a pumped dispersive fiber to produce a dispersed signal; amplifying the dispersed signal with an optical amplifier; detecting said amplified dispersed signal to produce an electrical signal; improving said electrical signal with an electrical filter and an electrical amplifier; digitizing said improved electric signal to provide a digital signal; and processing the digital signal to produce an image 11. A method according to embodiment 10, wherein said detection further comprises: correlation matching said dispersed signal against a database with a pattern generator and a amplitude modulator prior to detection.

12. A method for optical imaging, comprising generating a two-dimensional spectral brush with a two-dimensional disperser and a light source; exposing a sample to said two-dimensional spectral brush; measuring a transmitted spatial brush encoding spatial information of the sample to provide a transmitted spectral brush; decoding the transmitted spectral brush to provide an electric signal; and processing said electric signal to retrieve a two-dimensional image.

13. A method according to embodiment 12, where the transmitted spectral brush transmission comprises providing a light beam; transmitting the light beam through a first disperser to a sample to produce a first dispersed beam; transmitting the first disperse beam from said sample through a second disperser to produce a modified beam; and detecting said modified beam.

14. A method according to embodiment 13, where the light beam transmitted through the first disperser is transmitted through at least one orthogonally oriented coarse disperser and one fine disperser.

15. A method according to embodiment 13, where the first disperser and said second disperser are identical.

16. A method according to embodiment 12, where the transmitted spatial brush transmission comprises: providing a beam of light; directing the beam of light through a fiber collimator, beam expander and cylindrical lens to a course disperser and a fine disperser onto a sample; modulating light beams transmitted through said sample with a spatial light modulator; transmitting modulated light beams through a second course disperser and a second fine disperser to produce a modified beam; and refining said modified beam for detection by passing it through a cylindrical lens, telescope, fiber collimator, optical amplifier, pulse picker, optical filter, pumped dispersive fiber and second amplifier.

17. A method according to embodiment 16, further comprising matching optically detected signals with an image database with a 1-bit quantizer.

18. A method according to embodiment 12, further comprising reflecting the transmitted spectral brush with a mirror.

19. A method of optical imaging, comprising generating a two-dimensional spectral brush with a two-dimensional disperser and a light source; exposing a sample to said two-dimensional spectral brush at locations in a third dimension in succession; encoding spatial information of the sample into its spectrum in an interferometric configuration to provide a back reflected spectral brush image at each location; amplifying the back reflected spectral brush images; decoding each of the amplified back reflected spectral brush image with a decoder (spectrometer); processing each decoded brush image to retrieve final composite three-dimensional image.

20. A method according to embodiment 19, where the light source is selected from group of light sources consisting essentially of an incoherent light source, a broadband pulse laser light source and a swept frequency continuous-wave laser light source.

21. An apparatus for optical imaging, comprising: a light source; a spatial disperser operably coupled to the light source; a temporal disperser; an optical detector; and a digitizer.

22. An apparatus for optical imaging, comprising a broadband pulse laser; an optical circulator; a spatial disperser, a temporal disperser; an optical detector and a digitizer.

23. An apparatus according to embodiment 22 further comprising a digital signal processor, monitor and image storage.

24. An apparatus for optical imaging, comprising a broadband pulse laser; a pulse picker; an optical amplifier; a super-continuum generator; an optical filter; an optical circulator; a fiber collimator; a beam expander; a cylindrical lens; a spatial disperser, steering mirrors; objective lens; and optical amplifier; a temporal disperser; a dispersive fiber pump; an optical detector; an electric filter; an electrical amplifier a digitizer; a digital signal processor and a monitor.

25. An apparatus for optical imaging, comprising a function generator; a swept frequency continuous wave laser; an optical circulator; a spatial disperser, an optical detector; and a digitizer.

26. An apparatus for optical imaging, comprising a function generator; a swept frequency continuous wave laser; an optical amplifier; an optical filter; an optical circulator; a fiber collimator; a beam expander; a cylindrical lens; a spatial disperser, steering mirrors; objective lens; and optical amplifier; an optical detector; an electric filter; an electrical amplifier a digitizer; a digital signal processor and a monitor.

27. An apparatus according to embodiment 22 further comprising a beam combiner; an optical fiber and a second laser configured to image and ablate tissue simultaneously.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art. In any appended claims, reference to an element in the singular is not intended to mean "one and only one" unless explicitly so stated, but rather "one or more." All structural, chemical, and functional equivalents to the elements of the above-described preferred embodiments that are known to those of ordinary skill in the art are expressly incorporated herein by reference and are intended to be encompassed by the present disclosure. Moreover, it is not necessary for a device or method to address each and every problem sought to be solved by the present invention, for it to be encompassed by the present disclosure. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A method of optical imaging, comprising:
    generating a two-dimensional spectral brush by directing a beam of light through a fiber collimator, beam expander and cylindrical lens to a first coarse disperser and a fine disperser onto a sample;
    modulating light beams from the two-dimensional spectral brush transmitted through the sample with a spatial light modulator;
    transmitting modulated light beams through a second coarse disperser and a second fine disperser to produce a modified beam;
    refining the modified beam for detection by passing it through a cylindrical lens, telescope, fiber collimator, optical amplifier, pulse picker, optical filter, pumped dispersive fiber and second amplifier to produce a transmitted spatial brush encoding spatial information of the sample to provide a transmitted spectral brush;
    decoding the transmitted spectral brush to provide an electric signal; and
    processing said electric signal to retrieve a two-dimensional image.

2. A method as recited in claim 1, wherein said first disperser and said second disperser are identical.

3. A method as recited in claim 1, further comprising matching optically detected signals with an image database with a 1-bit quantizer.

4. A method as recited in claim 1, further comprising reflecting the transmitted spectral brush with a mirror.

5. A method as recited in claim 1, wherein said beam of light is produced by a light source selected from group of light sources consisting of an incoherent light source, a broadband pulse laser light source and a swept frequency continuous-wave laser light source.

6. A method as recited in claim 1, wherein said decoding comprises:
    performing a Dispersive Fourier Transformation on broadband laser pulses to provide temporal waveform;
    capturing said waveform;
    digitizing said captured waveform to provide a digital signal; and
    processing the digital signal to produce an image.

* * * * *